US010987067B2

(12) United States Patent
Fernando

(10) Patent No.: US 10,987,067 B2
(45) Date of Patent: Apr. 27, 2021

(54) WEARABLE EARPIECE OXYGEN MONITOR

(71) Applicant: OXIWEAR, INC., Arlington, VA (US)

(72) Inventor: Shavini Fernando, Arlington, VA (US)

(73) Assignee: OXIWEAR, INC., Arlington, VA (US)

( * ) Notice: Subject to any disclaimer, the term of this patent is extended or adjusted under 35 U.S.C. 154(b) by 0 days.

(21) Appl. No.: 16/903,732

(22) Filed: Jun. 17, 2020

(65) Prior Publication Data
US 2020/0390402 A1 Dec. 17, 2020

Related U.S. Application Data

(60) Provisional application No. 62/862,316, filed on Jun. 17, 2019.

(51) Int. Cl.
*A61B 5/1455* (2006.01)
*A61B 5/00* (2006.01)
(Continued)

(52) U.S. Cl.
CPC .......... *A61B 5/746* (2013.01); *A61B 5/0022* (2013.01); *A61B 5/01* (2013.01); *A61B 5/02427* (2013.01); *A61B 5/14552* (2013.01); *A61B 5/6803* (2013.01); *A61B 5/7405* (2013.01); *A61B 5/747* (2013.01); *A61B 5/7455* (2013.01);
(Continued)

(58) Field of Classification Search
None
See application file for complete search history.

(56) References Cited

U.S. PATENT DOCUMENTS 3,145,872 A   8/1964  Thomas
D209,789 S    1/1968  Huston
(Continued)

FOREIGN PATENT DOCUMENTS

CN       208799232 U      4/2019
WO    WO 2017/119638 A1   7/2017

OTHER PUBLICATIONS

International Search Report and Written Opinion dated Sep. 28, 2020, for International Application No. PCT/US2020/038146.

*Primary Examiner* — Eric F Winakur
*Assistant Examiner* — Marjan Fardanesh
(74) *Attorney, Agent, or Firm* — Cooley LLP

(57) ABSTRACT

An apparatus for monitoring an oxygen saturation level of a wearer of the apparatus includes a processor, a memory operably coupled to the processor, a first housing portion, a second housing portion, and a connection member. The first housing portion includes at least one light-emitting diode (LED), and the second housing portion includes a photodetector. The connection member is mechanically coupled to each of the first housing portion and the second housing portion. The apparatus is sized and shaped to be worn about a portion of an ear of a wearer of the apparatus. During operation, the at least one LED emits light in a direction toward the photodetector. A portion of the emitted light passes through the portion of the ear prior to arriving at the photodetector. The photodetector detects a signal in response to the portion of the emitted light, and the memory stores instructions to cause the processor to calculate an oxygen saturation level of the wearer based on the detected signal.

10 Claims, 47 Drawing Sheets

(51) Int. Cl.
  *A61B 5/01* (2006.01)
  *A61B 5/024* (2006.01)
  *H04W 4/38* (2018.01)
  *H04W 4/14* (2009.01)
  *H04W 4/90* (2018.01)
  *G08B 7/06* (2006.01)

(52) U.S. Cl.
  CPC .............. *G08B 7/06* (2013.01); *H04W 4/14* (2013.01); *H04W 4/38* (2018.02); *H04W 4/90* (2018.02); *A61B 2560/0247* (2013.01); *A61B 2560/0257* (2013.01); *A61B 2562/0233* (2013.01)

(56) References Cited

U.S. PATENT DOCUMENTS

| | | |
|---|---|---|
| D234,968 S | 4/1975 | Ervin |
| D260,134 S | 8/1981 | Bercu |
| D281,033 S | 10/1985 | Mohri |
| D333,560 S | 3/1993 | Miyashita et al. |
| D337,177 S | 7/1993 | Tiramani et al. |
| D350,757 S | 9/1994 | Carpenter |
| 5,830,137 A * | 11/1998 | Scharf ............... A61B 5/14551 600/323 |
| 6,497,495 B1 | 12/2002 | Janz |
| 6,580,800 B1 | 6/2003 | Yamasaki et al. |
| D485,390 S | 1/2004 | Stancik et al. |
| 6,677,078 B2 | 1/2004 | Reise et al. |
| D504,672 S | 5/2005 | Hirano |
| D512,982 S | 12/2005 | Rodarte |
| D515,069 S | 2/2006 | Naito |
| 7,010,137 B1 | 3/2006 | Leedom et al. |
| D551,216 S | 9/2007 | Wei |
| D586,935 S | 2/2009 | Lassen |
| D606,971 S | 12/2009 | Christopher et al. |
| D621,389 S | 8/2010 | Nagayama et al. |
| D633,899 S | 3/2011 | Zheng et al. |
| 7,983,437 B2 | 7/2011 | Wong et al. |
| D648,470 S | 11/2011 | Rains |
| D651,208 S | 12/2011 | Pacyga et al. |
| D652,817 S | 1/2012 | Lee et al. |
| D670,396 S | 11/2012 | Doogan |
| D671,096 S | 11/2012 | Song et al. |
| 8,345,912 B2 | 1/2013 | Akihiko et al. |
| D683,331 S | 5/2013 | Nylen |
| D698,026 S | 1/2014 | Kuwata et al. |
| D699,226 S | 2/2014 | Yoon |
| D708,377 S | 7/2014 | Osiecki et al. |
| 8,891,800 B1 | 11/2014 | Shaffer |
| 8,983,108 B2 | 3/2015 | Ho |
| D727,301 S | 4/2015 | Smith et al. |
| D740,223 S | 10/2015 | Yoneta |
| D740,786 S | 10/2015 | Huang et al. |
| D751,053 S | 3/2016 | Shin et al. |
| D756,971 S | 5/2016 | Park et al. |
| D758,901 S | 6/2016 | Benoit et al. |
| D771,599 S | 11/2016 | Kim |
| D783,422 S | 4/2017 | Kashimoto |
| D786,221 S | 5/2017 | Stoch |
| D801,312 S | 10/2017 | Birger |
| D809,664 S | 2/2018 | Ma et al. |
| D814,457 S | 4/2018 | Willis |
| D821,392 S | 6/2018 | Kwon et al. |
| D822,007 S | 7/2018 | Willis et al. |
| D835,286 S | 12/2018 | Sebban |
| D846,264 S | 4/2019 | Wu |
| D853,350 S | 7/2019 | Linden et al. |
| D853,358 S | 7/2019 | Damboulev et al. |
| D853,992 S | 7/2019 | Kuh et al. |
| D853,993 S | 7/2019 | Kuh et al. |
| D855,808 S | 8/2019 | Smith et al. |
| D863,261 S | 10/2019 | Zhu |
| D873,217 S | 1/2020 | Zhang |
| D880,458 S | 4/2020 | Minarsch et al. |
| D886,083 S | 6/2020 | Cho et al. |
| D890,136 S | 7/2020 | Cohen et al. |
| D891,774 S | 8/2020 | Yu |
| D892,770 S | 8/2020 | Gao |
| D894,123 S | 8/2020 | Xiong |
| 2009/0227852 A1 | 9/2009 | Glaser |
| 2011/0034783 A1* | 2/2011 | Lisogurski ........... A61B 5/0002 600/301 |
| 2012/0253159 A1 | 10/2012 | Medina et al. |
| 2014/0243617 A1* | 8/2014 | LeBoeuf ............. A61B 5/0084 600/301 |
| 2015/0305674 A1* | 10/2015 | McPherson ......... A61B 5/4875 600/301 |
| 2016/0081562 A1 | 3/2016 | Lachman |
| 2017/0094394 A1 | 3/2017 | McPeak et al. |
| 2019/0117159 A1* | 4/2019 | Peeters ............. A61B 5/02427 |
| 2019/0212198 A1* | 7/2019 | Marsh ..................... G01J 5/12 |

* cited by examiner

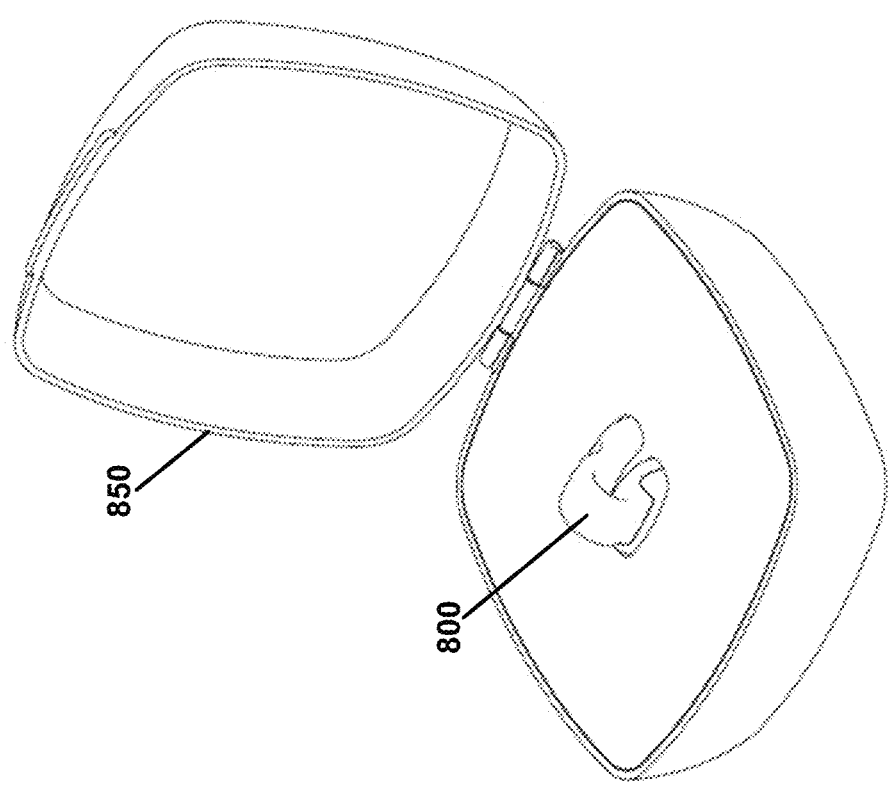
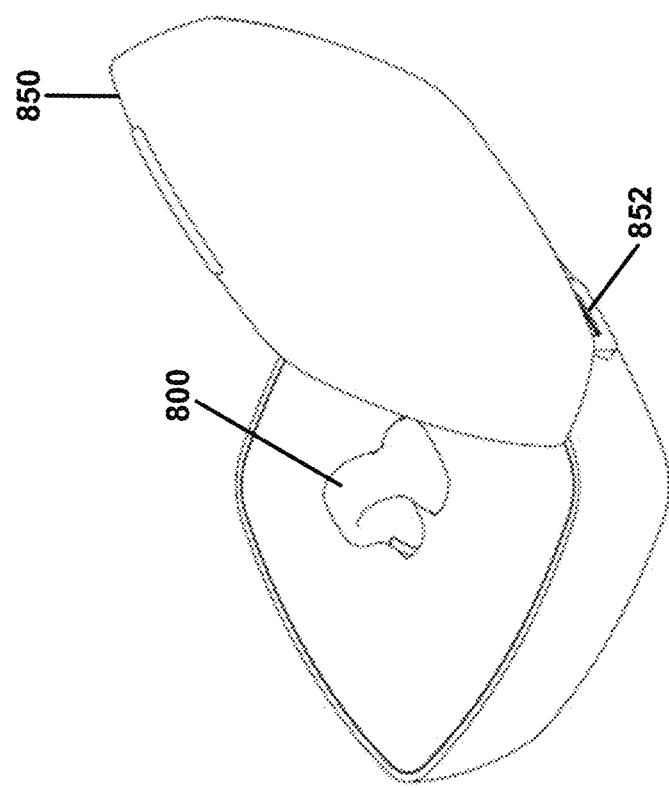

Dial 911 with the press of a button

Speak with 911 through your device

Welcome to Oxiwear

Continuous SPO2 Monitoring
SPO2 - amount of oxygen in the blood

FIG. 21

Settings

Alerts and Notifications

Location Services

Unit Preferences

Language Preference

App Sync

Personalization

Profile

| Name | Jane Doe |
|---|---|
| Age | 32 |
| Gender | Female |
| Weight | 125 |
| PH Class | 3 |
| Safe Threshold | 87-100 |
| Medication | |
| Allergies/Reactions | |

Journal

Date
Time

SPO2:  AQI:
HR:  Altitude:

Medication (add icon)

add medication

Symptoms (add icon)

add symptom

Notes (add icon)
click to add notes

Emergency Info

Emergency Contacts

---

Doctor's Notes click to add notes

---

Notes for EMS click to add notes

---

Select your Gender

Male        Female

*blurb about why this information is important

Next

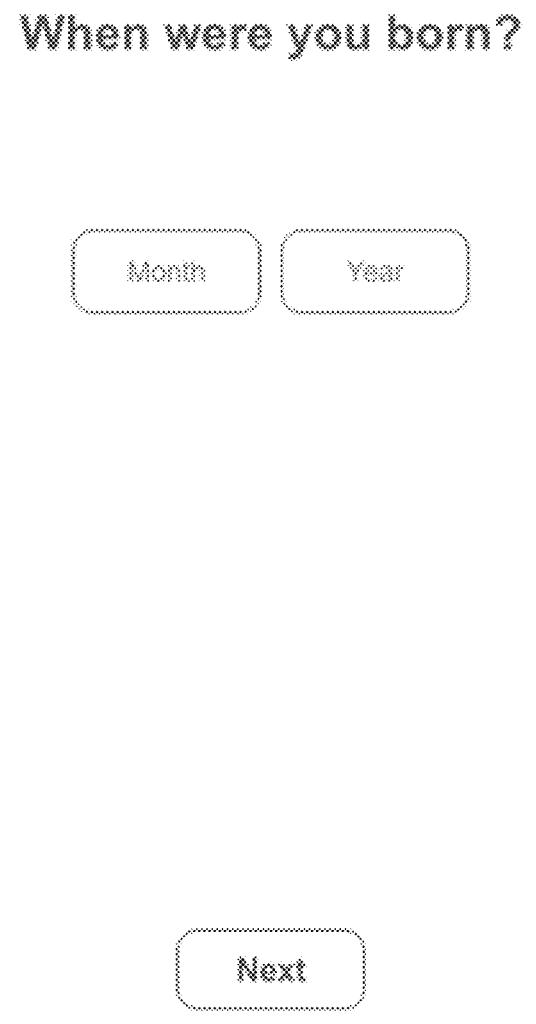

When were you born?

Month  Year

Next

FIG. 28

Do you have a
cardiovascular disease?

Yes   No

Next

FIG. 30

Do you have pulmonary hypertension (PH)?

Yes   No

Next

FIG. 32

Do you have pulmonary hypertension (PH)?

Yes   No

What World Health Organization class is your PH?

Group 1
pulmonary arterial hypertension

Group 2
PH due to left heart disease

Group 3
PH due to lung disease and/or chronic hypoxia

Group 4
PH due to blood clots in the lungs

Group 5
PH due to blood and other disorders

Next

FIG. 33

Date: Altitude:
Time: Air Quality Index:
SPO2: Barometric Pressure:
HR: Humidity:

Medication

*no medication added today*

Symptoms

*no symptoms added today*

Notes

*tap to add feelings or thoughts*

Dashboard  Reports  Medical ID  Progress  Journal

| | |
|---|---|
| Age | 32 |
| Gender | Female |
| Weight | 130 |
| PH Class | 3 |
| Safe Threshold | 87-100 |
| Medication | |
| Allergies/Reactions | |
| Emergency Contacts | |
| Doctor's Notes | |
| tap to add notes | |

Set Safe Threshold

WEARABLE EARPIECE OXYGEN MONITOR

CROSS-REFERENCE TO RELATED APPLICATIONS

This application claims priority to and the benefit of U.S. Provisional Patent Application No. 62/862,316, titled "Wearable Earpiece Oxygen Monitor," filed Jun. 17, 2019, the disclosure of which is hereby incorporated by reference in its entirety.

FIELD

The present disclosure relates to physiological monitoring technology, and more specifically, to the monitoring of an oxygen level of a wearer of a device.

BACKGROUND

Conditions such as pulmonary hypertension can be treated by providing the patient with supplemental oxygen therapy. The supplemental oxygen therapy can include delivering oxygen to the patient continuously, or during specific events such as exercise or sleep.

SUMMARY

An apparatus for monitoring a blood oxygen saturation level of a wearer of the apparatus includes a processor, a memory operably coupled to the processor, a first housing portion, a second housing portion, and a connection member. The first housing portion includes at least one light-emitting diode (LED), and the second housing portion includes a photodetector. The connection member is mechanically coupled to each of the first housing portion and the second housing portion. The apparatus is sized and shaped to be worn about a portion of an ear of a wearer of the apparatus. During operation, the at least one LED emits light in a direction toward the photodetector. A portion of the emitted light passes through the portion of the ear prior to arriving at the photodetector. The photodetector detects a signal in response to the portion of the emitted light, and the memory stores instructions to cause the processor to calculate a blood oxygen saturation level of the wearer based on the detected signal.

In some embodiments, an apparatus includes a processor, a memory operably coupled to the processor, at least one light-emitting diode, a photodetector, and multiple sensors. The apparatus is sized and shaped to mechanically attach to a portion of an ear of a wearer of the apparatus. The at least one light-emitting diode is configured, during operation, to emit light in a direction toward the photodetector, a portion of the emitted light passing through the portion of the ear prior to arriving at the photodetector. The photodetector is configured to detect a signal in response to the portion of the emitted light. The memory stores instructions to cause the processor to calculate a blood oxygen saturation level of the wearer based on the detected signal, and to store, in memory, a representation of the calculated blood oxygen saturation level and at least one measurement collected by the plurality of sensors.

In some embodiments, an apparatus includes a processor, a memory operably coupled to the processor, a light-emitting diode, and a photodetector. The apparatus is sized and shaped to mechanically attach to a portion of an ear of a wearer of the apparatus. The memory stores instructions to cause the processor to calculate a blood oxygen saturation level of the wearer based on a signal detected at the photodetector, the signal resulting from an emission of the at least one light-emitting diode. The memory also stores instructions to cause the processor to compare the calculated blood oxygen saturation level to a predetermined threshold blood oxygen saturation level, and to generate an alert in response to detecting that the calculated blood oxygen saturation level is lower than the predetermined threshold blood oxygen saturation level.

BRIEF DESCRIPTION OF THE DRAWINGS

FIGS. 8A-8B are renderings of views of a wearable oxygen monitor in a charging case, according to an embodiment.

FIGS. 9-45 are wireframes of user interface screens of a mobile app that interacts with a wearable oxygen monitor, according to some embodiments.

DETAILED DESCRIPTION

Figure 1A:
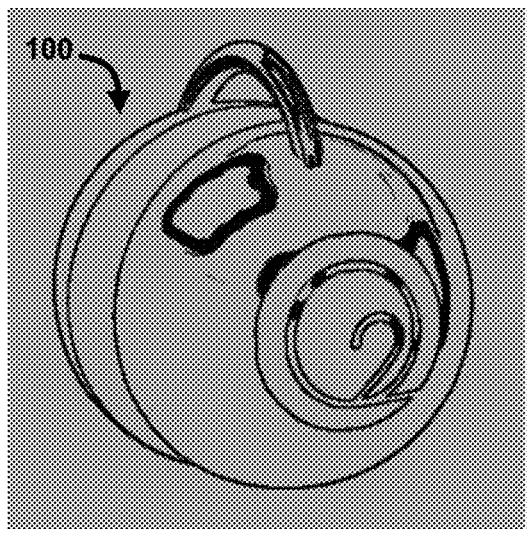
FIGS. 1A-1D are drawings of a wearable oxygen monitor, configured to be worn about a portion of an ear of a user, according to some embodiments.

Some health conditions, such as pulmonary hypertension (PH), pulmonary arterial hypertension (PAH) and idiopathic PAH (IPAH) are managed through the administration of oxygen and, relatedly, the monitoring of oxygen levels. Known devices for monitoring oxygen levels (such as pulse oximeters), however, are typically worn on the finger of a patient for discrete periods of time for measurement, and then taken off, for example because they are not designed or comfortable for continuous wear. Moreover, when a patient sleeps, he or she is not typically wearing a pulse oximeter, and is unable to view a digital readout of the pulse oximeter. As such, known pulse oximeters may not be effective for a notifying the patient of a critical drop in his or her oxygen level, for example while he/she sleeps, potentially leading to an exacerbation of the condition or even death. Moreover, known pulse oximeters do not include automated emergency detection and response capabilities. In other words, a user make take a voluntary action to measure his/her oxygen level, and upon determining that the level is too low, take another voluntary action to address it (e.g., call a doctor or emergency services using another device such as a telephone), if he/she is capable of doing so, potentially wasting valuable time.

Embodiments of the present disclosure include a wearable oxygen monitor that can be continuously worn and perform continuous oxygen monitoring and to alert a wearer/user when a detected oxygen level, detected during the oxygen monitoring, is lower than a predetermined or predefined threshold value. The wearable oxygen monitor can include an alert mechanism such as a button or touchscreen that, when interacted with by a user, initiates/activates one or more processes (e.g., stored in a memory of the wearable oxygen monitor and executable via a processor (e.g., a microprocessor) of the wearable oxygen monitor). The one or more processes can include an emergency plan. The emergency plan can include, but is not limited to, one or more of: contacting emergency services (e.g., initiating a telephone call to 911), sending a short message service (SMS) message (i.e., a text message) alert to a pre-programmed phone number (e.g., to a mobile device of the user or other designated person), emitting a sound from a sound emitter of the wearable oxygen monitor (e.g., an electronic beep sound effect emitted via a speaker), a vibration generated by a haptic feedback element of the wearable oxygen monitor (e.g., a piezoelectric transducer), transmitting (e.g., via a transceiver onboard the wearable oxygen monitor) a signal to a mobile device to cause an alert such as a sound effect and/or a vibration, etc.

In some embodiments, a wearable oxygen monitor is configured to dial 911 (or other emergency service) in response to button press (or other interaction with an alert mechanism) made by a wearer/user, for example as part of a defined emergency plan. The wearable oxygen monitor can also include a speaker and microphone such that the oxygen monitor functions as a headset. For example, the wearer/user can hear the voice of the emergency response dispatcher via the speaker of the wearable oxygen monitor, and the wearer/user can speak to the emergency response dispatcher via the microphone of the wearable oxygen monitor. In some implementations, in response to the button press and in addition to dialing 911, the wearable oxygen monitor can be configured to concurrently trigger the generation and sending (e.g., via a wireless communication channel) of an alert text message to one or more emergency contact numbers (e.g., three separate emergency contact numbers) stored in a memory of the wearable oxygen monitor and/or accessible by the wearable oxygen monitor via a mobile software application thereof. The alert text message(s) can include one or more of: an alert message, vital signs/biometrics of the wearer/user, and an indication that 911 has been called.

In some embodiments, a wearable oxygen monitor is in the form of a wearable, hardware-based earpiece that is sized and shaped to fit and be worn about a portion of a wearer's ear (e.g., a helix, scapha, pinna, or any other portion of the external ear). The earpiece can clip onto, mechanically attach to, or otherwise grip the portion of the ear. For example, the earpiece include a gap or recess, defined therein, that is sized and shaped to receive the portion of the ear. When the ear portion is inserted into or received by the gap or recess, the earpiece can be configured to exert a bias or spring force that provides a squeezing action about the ear portion, such that the earpiece is securely retained on the wearer's ear. The wearable oxygen monitor can include one or more of: one or more light-emitting diodes (LEDs), one or more photosensors/photodetectors, one or more lightweight, power-efficient, wireless sensors (e.g., temperature sensor(s), pressure sensor(s), accelerometer(s), GPS sensor(s), etc.), a speaker, a microphone, a processor and a memory operably coupled to the processor. The memory stores instructions executable by the processor during operation. During operation, the one or more LEDs (e.g., red and/or green LEDs) can emit light through the portion of the ear, and the light transmitted through the portion of the ear can be detected at the one or more photosensors/photodetectors. One or more biometrics or vital signs can then be calculated (e.g., blood oxygen level, blood oxygen saturation (SpO2), heart rate, body temperature, pulse rate, respiration rate, blood pressure, hydration, etc.) based on the amount of light that is detected at the one or more photosensors/photodetectors and/or based on an amount of light that is absorbed by the ear (and, thus, does not reach the one or more photosensors/photodetectors). For example, blood oxygen saturation (SpO2) can be calculated based on the amount of light that is absorbed by the ear and using Beer's law (also referred to as the Beer-Lambert law, which states that absorbance is proportional to the concentration of one or more attenuating species in a material sample). In some implementations, an accuracy of the determination of the blood oxygen saturation increases with the thickness of the portion of the ear on which the wearable oxygen monitor is positioned during operation.

In some embodiments, the one or more LEDs include two LEDs—a first LED being a red (650 nm) LED and a second LED being an infrared (950 nm) LED. During operation, when light from each of the two LEDs passes through an adjacent portion of the ear, light emitted from the first (red) LED is partially absorbed by deoxyhemoglobin of the portion of the ear, and light emitted from the second (infrared) LED is partially absorbed by oxyhemoglobin of the portion of the ear (the amounts of which can be determined based on the detected light at the photodector(s)/photosensor(s)). An oxygen concentration can then be calculated/detected, e.g., based on the ratio between the amount of light absorbed by deoxyhemoglobin and the amount of light absorbed by oxyhemoglobin. In some embodiments, the one or more LEDs includes at least one red and/or infrared LED for detecting a blood oxygen concentration of the wearer, and at least one green LED for detecting a pulse of the wearer. In some implementations, the determination of a blood oxygen concentration includes an adjustment to the detected signal (e.g., at the photodetector/photosensor) to correct for ambient or environmental light, such as sunlight. The adjustment can be based on an additional light sensor positioned, for example, on an outer surface of the wearable oxygen monitor. Such adjustments can be made, for example, when the wearable oxygen monitor is worn outdoors and/or in The memory can communicate with/via and/or store a software application that is compatible with one or more mobile devices (e.g., Windows, iOS, Android). The wearable oxygen monitor can be lightweight, power-efficient, and configured to communicate with one or more mobile devices and/or software application using one or more wireless communications protocols (e.g., Bluetooth®, 4G®, 5G®, etc.). The wearable oxygen monitor earpiece can include a power source that is rechargeable by a wired or wireless charging pod. The charging of the earpiece can occur when the earpiece is received at least partially within the charging pod and, optionally, when in electrical contact therewith.

In some embodiments, an emergency plan is activated in response to the wearer interacting with (e.g., pressing, tapping, sliding, etc.) the alert mechanism a predetermined number of times (e.g., once, twice, three times, four times, etc.) and/or with a predetermined frequency (e.g., three rapid taps within 1-5 seconds of each other). For example, a wearer pressing a button on the wearable oxygen monitor three times can trigger implementation/deployment of the emergency plan.

In some embodiments, a wearable oxygen monitor is configured to communicate connected (e.g., via wireless network communication) with a software application running on a mobile device (e.g., a smartphone, tablet, laptop computer, etc.) of a user/wearer of the wearable oxygen monitor or other individual. The software application can include code to cause storage of all vital records (e.g., blood oxygen level, heartrate/pulse, body temperature, hydration level, etc.) detected by one or more sensors onboard the wearable oxygen monitor, for example so that they can be sent to or shown to a medical provider. Alternatively or in addition, the software application can facilitate the definition/setting/customization, e.g., by a wearer/user of the wearable oxygen monitor or other authorized individual, of one or more set points or thresholds. The one or more set points or thresholds can include oxygen levels that will trigger an alert or alarm. Alternatively or in addition, the software application can facilitate the definition/setting/customization, e.g., by a wearer/user of the wearable oxygen monitor or other authorized individual, of one or more emergency contact telephone numbers to which an SMS message will be sent and/or that will be called when an alert/alarm is triggered.

In some embodiments, a wearable oxygen monitor includes a processor and a memory operably coupled to the processor. The memory stores instructions executable by the processor during operation. The instructions can include instructions to calculate an oxygen concentration, for example continuously and/or at predetermined intervals of time (e.g., every second, every 2 seconds, every 3 seconds, every 4 seconds, every 5 seconds, every 6 seconds, every 7 seconds, every 8 seconds, every 9 seconds, every 10 seconds, every 11 seconds, every 12 seconds, every 13 seconds, every 14 seconds, every 15 seconds, every 16 seconds, every 17 seconds, every 18 seconds, every 19 seconds, every 20 seconds, every 21 seconds, every 22 seconds, every 23 seconds, every 24 seconds, every 25 seconds, every 26 seconds, every 27 seconds, every 28 seconds, every 29 seconds, every 30 seconds, every 45 seconds, every minute, every 5 minutes, every 10 minutes, every 15 minutes, every 30 minutes, etc.).

The time interval can be configurable by a wearer/user of the wearable oxygen monitor and/or another authorized user, for example via a software application running on a mobile device of that individual and via wireless communication with the wearable oxygen monitor. In some implementations, the instructions include instructions to compare measured oxygen concentration levels (as measured by the wearable oxygen monitor) with a predetermined threshold value stored within the memory of the wearable oxygen monitor. The predetermined threshold value can be configurable by a wearer/user of the wearable oxygen monitor and/or another authorized user, for example via the software application.

In some embodiments, a wearable oxygen monitor is configured to emit an alarm sound and/or vibration in response to detecting that an oxygen level of a wearer/user is lower than a defined threshold value (e.g., representing an "alarm state"). An intensity, volume and/or frequency of the alarm sound and/or vibration can increase over time until the alarm is acknowledged by the wearer/user (e.g., via interaction of the wearer/user with an alert mechanism of the wearable oxygen monitor or via a graphical user interface (GUI) rendered by a software application of a mobile device of the wearer/user. Alternatively or in addition, an intensity, volume and/or frequency of the alarm sound and/or vibration can increase with and/or in proportion to an increase in a calculated difference between the detected oxygen level and the defined threshold value, such that the increasing intensity, volume and/or frequency of the alarm sound and/or vibration represents an increasing severity of the alarm state. Similarly, the intensity, volume and/or frequency of the alarm sound and/or vibration can decrease with and/or in proportion to a decrease in a calculated difference between the detected oxygen level and the defined threshold value, such that the increasing intensity, volume and/or frequency of the alarm sound and/or vibration represents a decreasing severity of the alarm state. The wearable oxygen monitor can terminate the alarm sound and/or vibration upon detection that a current oxygen level is equal to or greater than the defined threshold value.

In some embodiments, oxygen levels detected by (and, optionally, other sensor data gathered by/detected at) the wearable oxygen monitor are stored locally (e.g., within a memory of the wearable oxygen monitor) and/or are transmitted (e.g., via a transceiver of the wearable oxygen monitor) to a cloud-based server or other storage repository, for example using a software application. The wearable oxygen monitor, the cloud-based server and/or a software application associated with the wearable oxygen monitor can be configured to analyze sensor data collected/detected at the wearable oxygen monitor, for example to determine one or more conditions or biometric parameters based on the sensor data, to detect patterns associated with the sensor data over time, etc. Data stored locally and/or transmitted can include, in addition to the detected oxygen levels and optional other sensor data, information such as time and date of detection events associated with such data, an identifier of the earpiece, an identifier associated with the wearer, etc. Data stored at the cloud-based server can be downloaded therefrom by the wearer/user and/or other authorized person, for example to show a physician for purposes of diagnosis, investigation of anomalous events, etc. The ability of the wearer/user to download data from the cloud-based server can be limited, for example, to daily or weekly. Alternatively or in addition, a user may send a request to the cloud-based server, the request including a query specifying a range of dates for which he/she would like to retrieve data. Although described herein as pertaining to oxygen levels, systems and methods of the present disclosure can, alternatively or in addition, be used to detect other biometrics or vital signs, such as heartrate/pulse, body temperature, hydration level, salt level, etc.

In some embodiments, a mobile software application is configured for use with one or more wearable oxygen monitors of the present disclosure. The mobile software application can be compatible with one or more of Android, iOS and Windows, and can facilitate continuous communication between one or more mobile devices running the mobile software application and a wearable oxygen monitor (e.g., via one or more wireless sensors of the wearable oxygen monitor). The mobile software application can be configured to record/store detected vital s/biometric information (e.g., continuously, periodically, intermittently, and/or upon request or user interaction therewith) and, optionally, upload the detected data to a cloud-based storage for future reference. The mobile software application can be configured to send and/or receive a signal to cause display, e.g., in a GUI of a mobile device of the wearer/user, of one or more of the detected data values (and/or graphical representations thereof, for example over time), for example including oxygen levels, heart rate, etc. The mobile software application can be configured to identify and/or cause storage (e.g., in a database or other repository) of geometrics (e.g., geographic data such as GPS data) and/or barometrics (e.g., environmental data such as barometric pressure) in addition to the biometric information detected by the wearable oxygen monitor(s), and/or to track the occurrence of acute/emergency events over time (e.g., as indicated by the triggering of the emergency plan). Data received and/or stored by the software application can include crowd-sourced data (e.g., from multiple different wearable oxygen monitors associated with multiple different wearers, optionally without including identifying information associated with the individual wearers).

In some embodiments, data detected by one or more wearable oxygen monitors and information derived from such data is stored in a common repository and used to train a machine learning (ML) or artificial intelligence (AI) algorithm. The trained ML/AI algorithm can be used to predict future acute/emergency events (i.e., to perform predictive analytics), for example based on current (contemporaneous) sensor readings detected at the wearable oxygen monitor of a particular wearer. When a future acute/emergency event is predicted, an "early warning" alert can be generated and presented to a wearer/user (e.g., via a GUI of the wearer's mobile device, via the software application running thereon) such that the wearer/user can take remedial or preventative action (e.g., increase an oxygen intake).

Figure 1B:
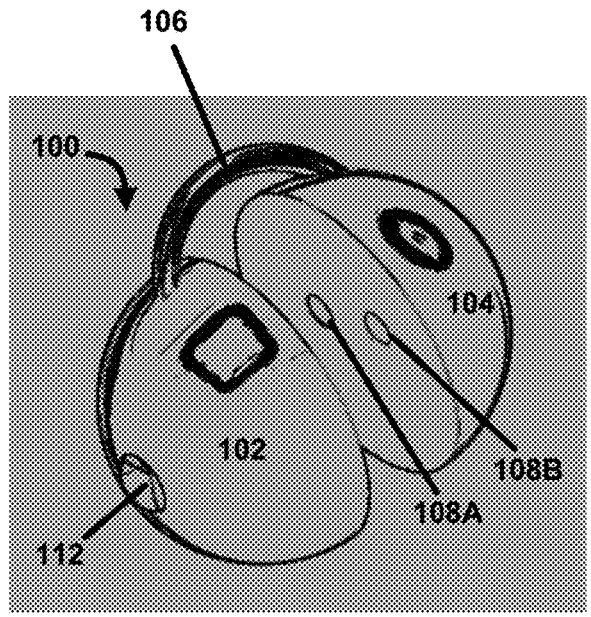
Figure 1C:
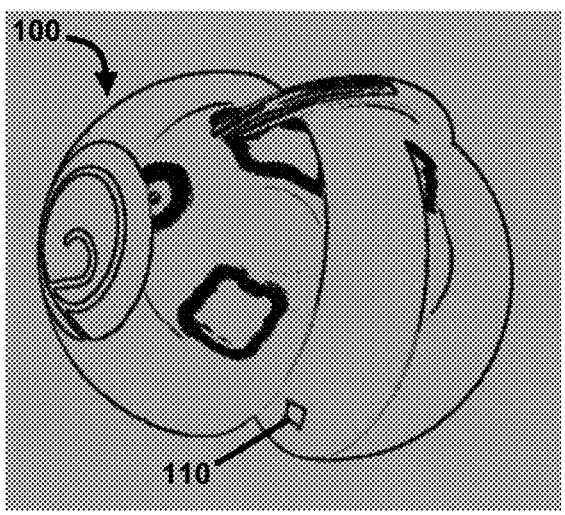
Figure 1D:
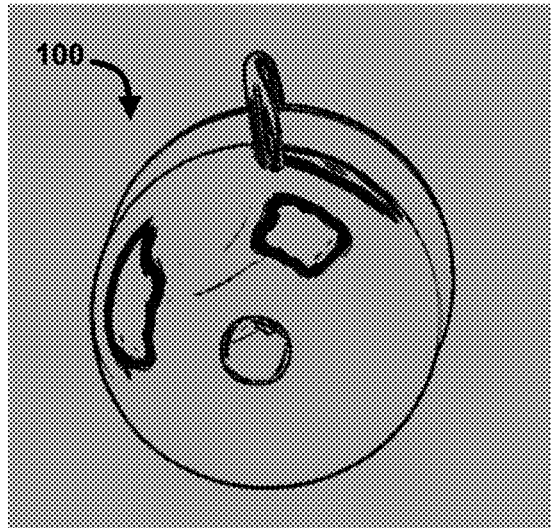

FIGS. 1A-1D are drawings of a wearable oxygen monitor, configured to be worn about a portion of an ear of a user, according to some embodiments. As shown in FIG. 1B, the wearable oxygen monitor 100 includes a first housing portion 102, a second housing portion 104, a first light-emitting diode (LED) 108A, a second LED 108B, an alert mechanism (e.g., a button) 112, and a connection member 106 that is mechanically coupled to each of the first housing portion 102 and the second housing portion 104. Each of the first housing portion 102 and the second housing portion 104, or portions thereof, can be removable and replaceable with replacement housing "skins" having a different appearance (e.g., color, texture, pattern), for example for customization of the appearance of the wearable oxygen monitor 100. Alternatively or in addition, the wearable oxygen monitor 100 can be compatible with one or more housing portion overlays ("skins") that can be fitted onto one or both of the first housing portion 102 and the second housing portion 104. In other words, a separate skin overlay can be configured to mechanically receive (or fit over) all or a portion of first housing portion 102 or the second housing portion 104, for customization of the appearance of the wearable oxygen monitor 100.

Figure 2B:
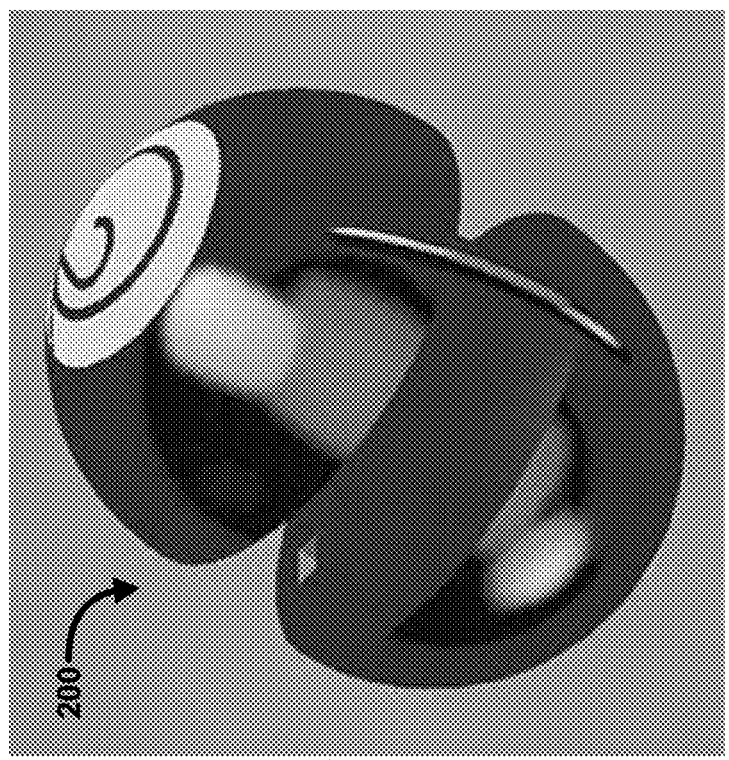
FIGS. 2A-2D are renderings of a wearable oxygen monitor, configured to be worn about a portion of an ear of a user, according to some embodiments.
Figure 2A:
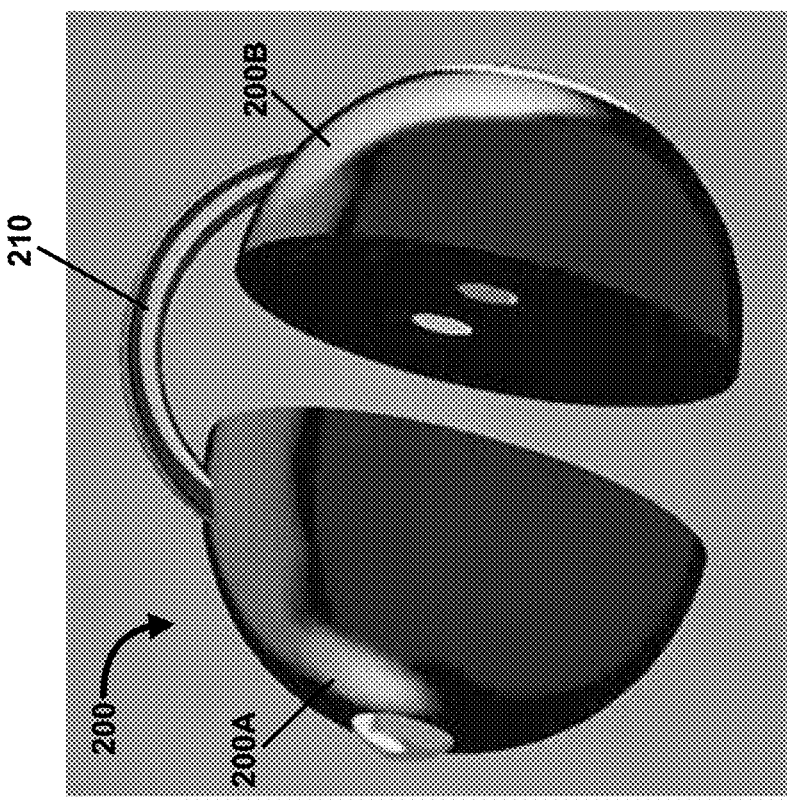
Figure 2D:
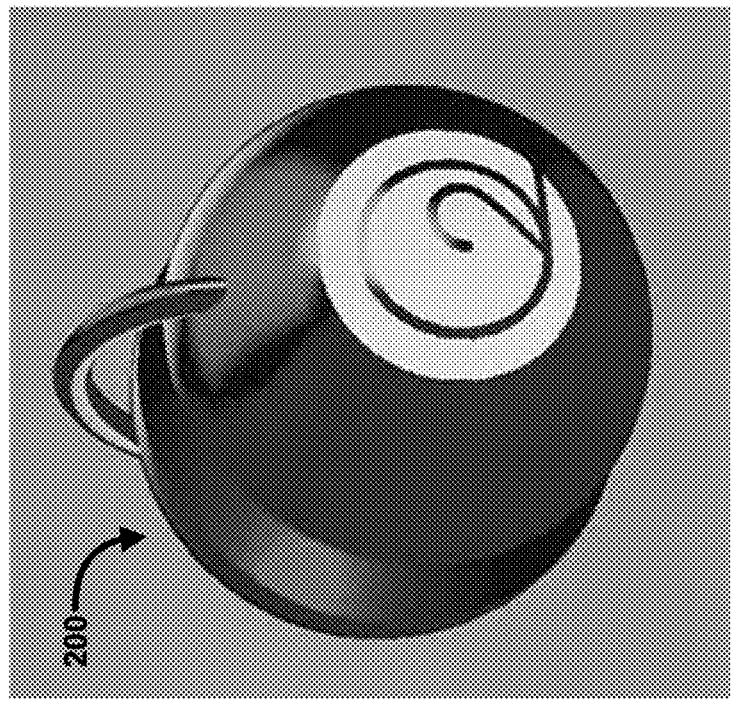
Figure 2C:
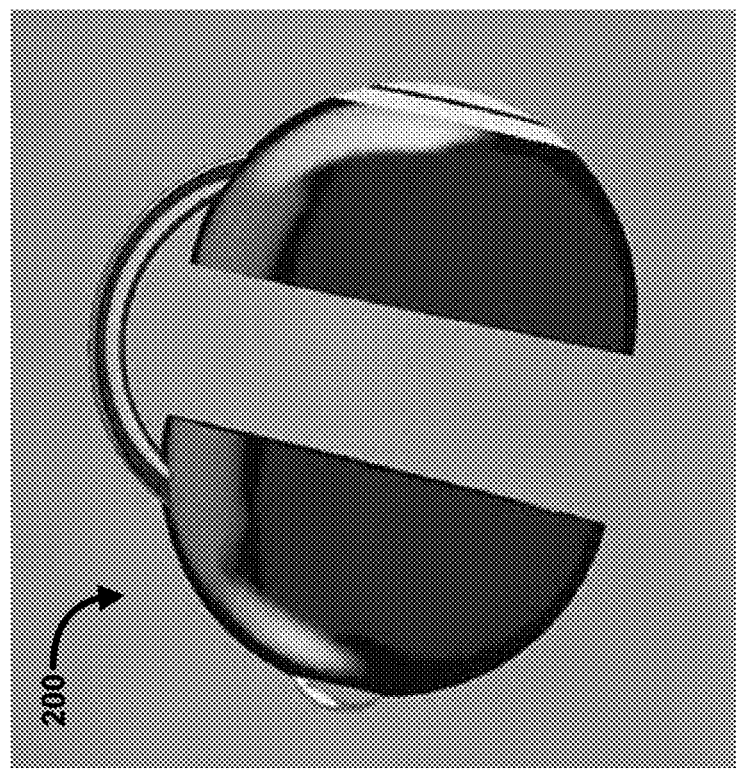

FIGS. 2A-2D are renderings of a wearable oxygen monitor 200, configured to be worn about a portion of an ear of a user, according to some embodiments. As shown in FIG. 2A, the wearable oxygen monitor 200 includes a first body portion 200A (e.g., having a substantially hemispherical shape) and a second body portion 200B (e.g., having a substantially hemispherical shape) that are mechanically (and, optionally, electrically) connected one another via a connecting member 210 (e.g., a "hook"). The first body portion 200A and the second body portion 200B, when the wearable oxygen monitor 200 is in an unworn state (e.g., when charging), there is a gap between the first body portion 200A and the second body portion 200B (a "first configuration"). The gap can be, for example, about 1 millimeter (mm), about 2 mm, about 3 mm, about 4 mm, about 5 mm, about 6 mm, about 7 mm, about 8 mm, about 9 mm, about 10 mm, or between any two of the foregoing values. The connecting member 210 can include a metal, and the gap is expandable for positioning of the wearable oxygen monitor about the portion of the ear of the user.

In some embodiments, during placement or "donning" of the wearable oxygen monitor 200, the gap can be expanded by, e.g., by moving the first body portion 200A and the second body portion 200B away from one another, expanding the radius of curvature of the connecting member 210, and/or deforming the connecting member 210. Once positioned on the portion of the ear of the user (a "second configuration"), and external force(s) are removed from the wearable oxygen monitor 200, the first body portion 200A and the second body portion 200B may naturally move a distance, equal to, a portion of the gap, toward one another, e.g., by virtue of a shape memory or an inherent spring force of the connecting member 210, such that the wearable oxygen monitor 200 remains securely positioned on the portion of the ear of the user during use (e.g., during movement of the user).

Figure 3:
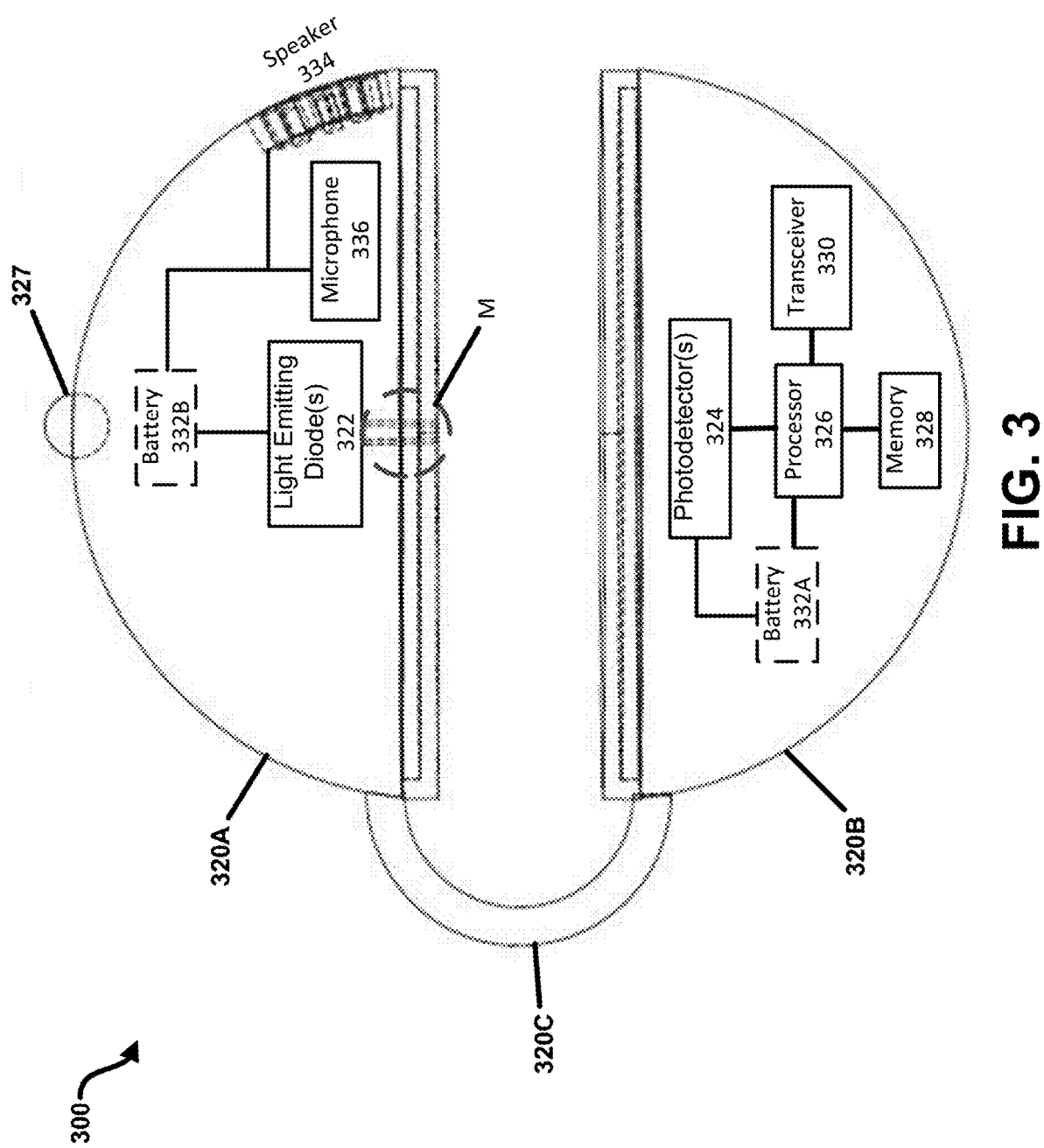
FIG. 3 is a schematic drawing showing components of a wearable oxygen monitor, according to some embodiments.

FIG. 3 is a cross-sectional schematic drawing showing internal components of a wearable oxygen monitor, according to some embodiments. As shown in FIG. 3, the wearable oxygen monitor 300 includes a first housing portion 320A (having a substantially hemispherical shape), a second housing portion 320B (having a substantially hemispherical shape), and a connection member 320C mechanically coupled to each of the first housing portion 320A and the second housing portion 320B. The wearable oxygen monitor 300 optionally includes a power ("ON"/"OFF") button (not shown). The first housing portion 320A includes one or more LEDs 322 (optionally in a row or array), a speaker 334, and a microphone 336, each optionally electrically coupled to a battery 332B or other power source and/or optionally electrically coupled, via an electrical conduit extending from the first housing portion 320A via the connection member 320C to a battery 332A of the second housing portion 320B. The first housing portion 320A also includes an alert mechanism (e.g., an actuatable button) 327 that is electrically connected to one of the battery 332A or the battery 332B, and is operably coupled to at least one of the processor 326 and the transceiver 330. The second housing portion 320B includes one or more photodetectors 324, a processor 326 operably coupled to a memory 328, and a transceiver 330 operably coupled to the processor 326 and configured to send and/or receive communications (e.g., to/from a remote compute device such as a mobile device of a wearer/user of the wearable oxygen monitor 300 or other authorized person), for example including data gathered by the one or more photodetectors 324 and/or processor 326, and/or stored in the memory 328. The processor 326 is operably coupled to, and configured to control (e.g., based on processor-executable instructions stored in the memory 328 and/or received via the transceiver 330) at least one of the one or more LEDs 322, the microphone 336, the speaker 334, or the battery 332B, via an electrical conduit (not shown) extending from the first housing portion 320A via the connection member 320C to the second housing portion 320B, and/or the battery 332B. Each of the photodetectors 324, the processor 326, and the transceiver 330 is optionally electrically coupled to the battery 332A or other power source and/or optionally electrically coupled, via an electrical conduit (not shown) extending from the second housing portion 320B via the connection member 320C to the battery 332B of the first housing portion 320A. During operation, and when worn about a portion of an ear of the wearer/user, the one or more LEDs 322 emit light via one or more passages/orifices "M"

such that the emitted light partially passes through (i.e., transmits) and is partially absorbed within the portion of the ear and in a direction toward the one or more photodetectors 324. The one or more photodetectors 324 detect a signal in response to the emitted light. In some implementations, the processor 326 determines an oxygen level of the wearer based on the detected signal and, optionally, stores the determined oxygen level in the memory 328, optionally with date information, time information, and/or other sensor data detected based on one or more other sensors (not shown) onboard the wearable oxygen monitor 300. Alternatively or in addition, raw data including the detected signal (optionally with data detected using the one or more other sensors) can be sent, via the processor 326 and using the transceiver 330, to a remote compute device such as a cloud-based server, a remote mobile device, etc., for determination of an oxygen level based on the raw data. Although shown and described, with respect to FIG. 3, to be in particular portions (first housing portion 320A or second housing portion 320B) of the wearable oxygen monitor 300, any component or combination of components of the wearable oxygen monitor 300 (i.e., LED(s) 322, microphone 336, speaker 334, battery 332A, battery 332B, photodetector(s) 324, processor 326, transceiver 330, and/or memory 328) can alternatively be positioned in the first housing portion 320A, the second housing portion 320B, or both, depending upon the particular embodiment.

Figure 4:
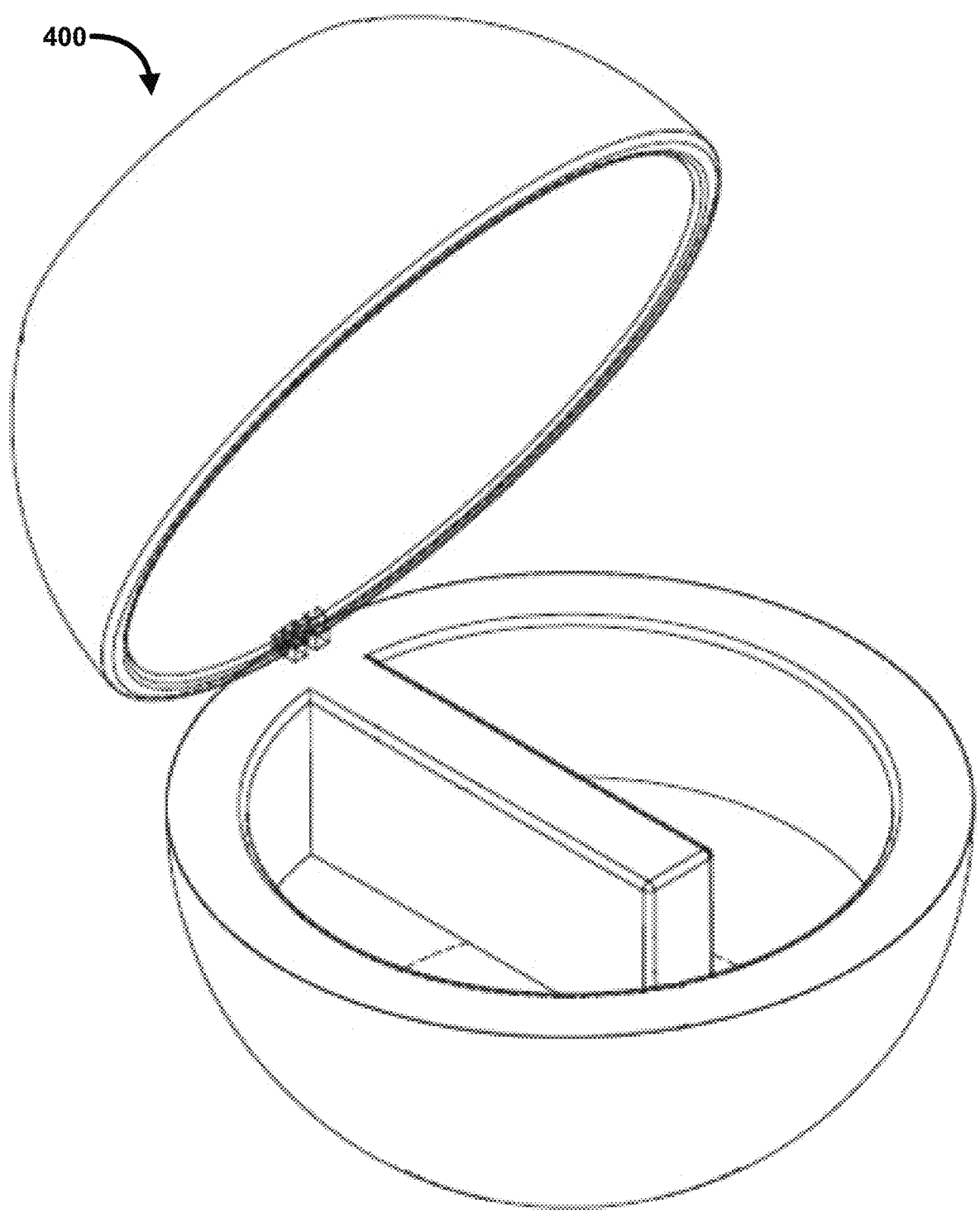
FIG. 4 is a schematic drawing of a charger for a wearable oxygen monitor, according to some embodiments.
Figure 5:
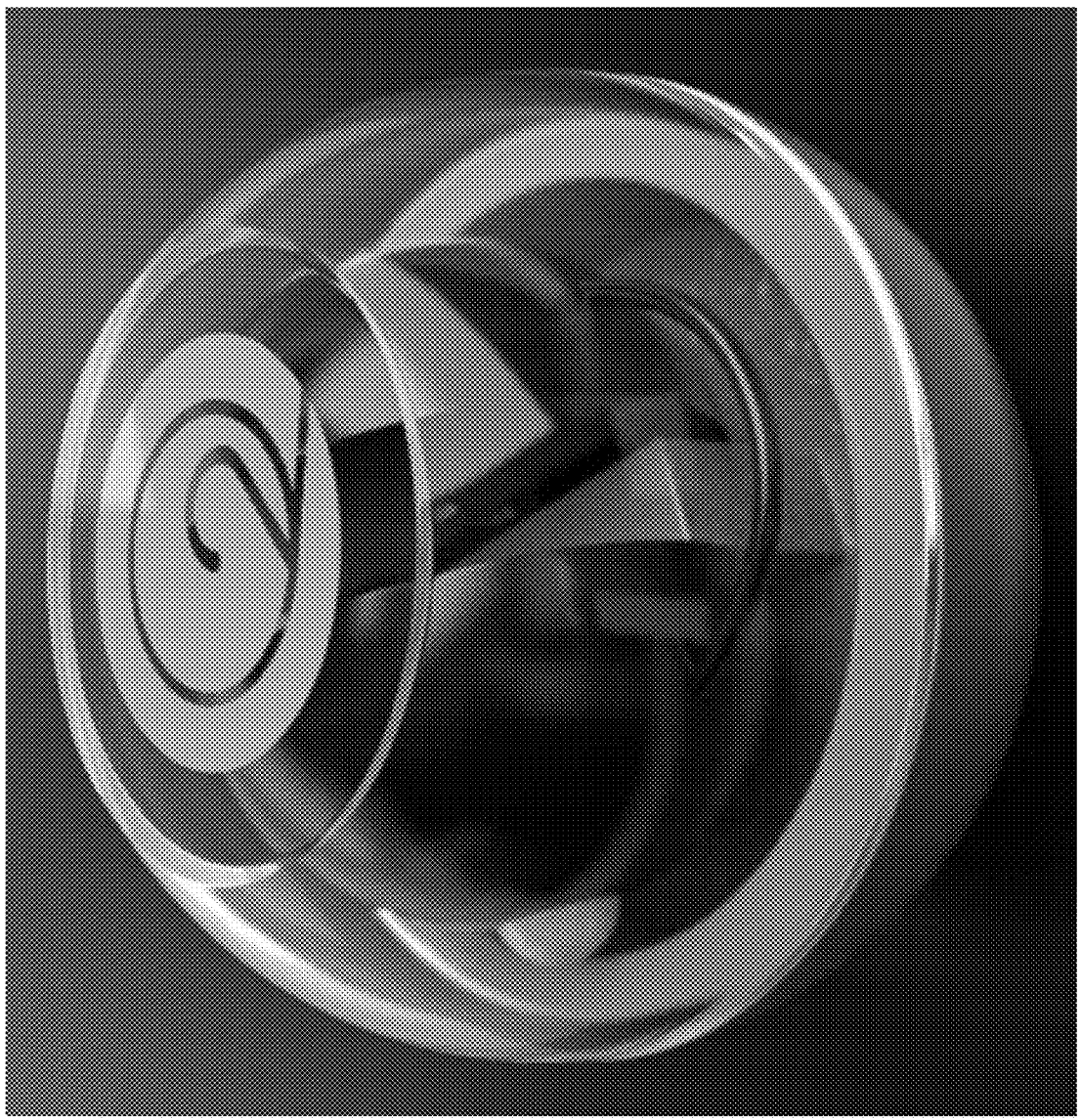
FIG. 5 is a rendering of a charging case for a wearable oxygen monitor with the wearable oxygen monitor disposed therein, according to some embodiments.

FIG. 4 is a schematic drawing of a charger for a wearable oxygen monitor 400, in an open configuration, according to some embodiments. FIG. 5 is a rendering of a charger similar to the charger of FIG. 4, with the wearable oxygen monitor earpiece disposed therein (500), according to some embodiments. The charging of the earpiece can occur when the earpiece is received at least partially within the charging pod and, optionally, when in electrical contact therewith. As shown in FIGS. 4 and 5, the charger can include a partition about which the earpiece is positioned when in a charging configuration. In some embodiments, the wearable oxygen monitor 300 and/or the charger for the wearable oxygen monitor 400 includes an external "skin" or "housing" that is removable, such that a replacement skin or housing (e.g., having a different appearance, such as color, texture, pattern, etc.) can be substituted for an original skin or housing.

Wearable oxygen monitors of the present disclosure, according to some embodiments, can include one or more (e.g., any combination) of the following capabilities:

Continuous oxygen monitoring;
Heart rate monitoring;
Generating and sending alerts;
Activation of a pre-defined emergency plan;
Interaction with a mobile software application; and/or
Predictive analytics.

In some embodiments, a wearable monitoring system includes a wearable oxygen monitor and a mobile software application ("mobile app") running on a compute device of a user or wearer of the wearable oxygen monitor. During operation of the wearable oxygen monitor (i.e., when the wearable oxygen monitor is powered on and being worn by the wearer), the wearable oxygen monitor can continuously monitor the oxygen level of the wearer, for example by comparing a measured oxygen level to a pre-defined oxygen level threshold. Based on the monitoring, and in response to detecting that a measured oxygen level is less than the pre-defined oxygen level threshold, the wearable oxygen monitor can generate an alert, the alert including a representation of the low oxygen condition, and send a signal representing the alert to the mobile app to cause an alert (including one or more of text, graphics, video indications, and audio indications) to be displayed and/or played by the mobile app and the compute device (e.g., via a graphical user interface (GUI) of the compute device and/or one or more speakers thereof).

In some embodiments, during operation, the wearable oxygen monitor detects data associated with one or more physiological conditions of the wearer (collectively referred to herein as "vital signs"), including, but not limited to, oxygen level, heart rate, etc., for example at multiple instances over time. The wearable oxygen monitor can, in response to detecting the vital signs, store the vital signs in a memory of the wearable oxygen monitor. Alternatively or in combination, the wearable oxygen monitor can send a signal representing the vital signs to one or more remote compute devices (e.g., a mobile compute device of a user or the wearer, optionally running the mobile app) for storage and/or display (e.g., via a GUI). The vital signs can subsequently be accessible and retrievable by the wearer or user. In addition, the wearer can provide access to the vital signs to a medical practitioner, for example by providing the medical practitioner with access credentials (for the wearable oxygen monitor and/or the mobile app) and/or by generating and sending (via the mobile app) an email or other message, including a representation of the vital signs, to the medical practitioner.

In some embodiments, a wearable monitoring system includes a wearable oxygen monitor and a mobile app running on a compute device of a user or wearer of the wearable oxygen monitor. The wearable monitoring system is configured to generate and send one or more alerts when a vital sign is determined not to comply with a predetermined condition (optionally customizable by the wearer/user). For example, the wearable monitoring system (e.g., the wearable oxygen monitor and/or the mobile app) can be configured to generate and send one or more alerts when an oxygen level, measured by the wearable oxygen monitor, drops below a pre-defined (optionally customizable) level (also referred to herein as a "trigger" or "threshold value"). In addition, the wearable monitoring system can be configured to generate and send one or more alerts in response to when the user/wearer presses an alert mechanism (e.g., an actuatable button) on the wearable oxygen monitor, or otherwise interacts with the wearable oxygen monitor (examples of which include, but are not limited to, voice command, rotation of a component of the wearable oxygen monitor, sliding of a component of the wearable oxygen monitor, pressing or squeezing a component of the wearable oxygen monitor (e.g., for a predefined duration, with a predefined amount of force, a predetermined number of times in succession (e.g., 3 times), in a predefined pattern, etc.), removal of a component of the wearable oxygen monitor, removal of the entirety of the wearable oxygen monitor from the ear of the wearer, etc.).

The one or more alerts can include a representation of a "low oxygen" condition and/or an associated instruction to execute one or more commands, such as initiating a telephone call (e.g., via the mobile device running the mobile app) to, or otherwise contacting, emergency services (e.g., 911), sending an SMS, email or other message to one or more emergency contacts, emitting a sound from a sound emitter of the wearable oxygen monitor (e.g., an electronic beep sound effect emitted via a speaker), causing a vibration to be generated by a haptic feedback element of the wearable oxygen monitor (e.g., a piezoelectric transducer), transmitting (e.g., via a transceiver onboard the wearable oxygen monitor) a signal to a mobile device to cause an alert such as a sound effect and/or a vibration, etc. The user or wearer can, via the mobile app, define customized values for one or more of the following: threshold oxygen level(s), detection intervals (e.g., for oxygen levels, blood oxygen saturation levels, or other vital signs), frequency of calculation of vital signs (e.g., to calculate oxygen concentration at 1-30 second time intervals), threshold values for other vital signs and/or biometrics, emergency contact information (e.g., phone numbers, email addresses, names, etc.), emergency plan data, priority order of vital signs, priority order of emergency contacts, access permissions for healthcare providers, etc.

In some embodiments, the wearable monitoring system includes a predictive analytics capability and/or interacts with a predictive analytics system, to provide advance warnings ("pre-warnings") to the wearer or user before an acute health episode occurs, for example by identifying/detecting patterns based on previous acute health episodes of the wearer/user. The predictive analytics capability can be implemented using software (e.g., artificial intelligence (AI), machine learning, or other algorithms) and/or hardware. The identifying/detecting the patterns can be performed by analyzing biometric data (including vital signs and/or other data detected and/or gathered by the wearable monitoring system), optionally in combination with geometric data and/or barometric data collected using the wearable monitoring system. For example, collected geometric data and/or barometric data can be compared with historical data pertaining to occurrences of low oxygen alerts/warnings and/or invocations of emergency services (e.g., 911 calls) to identify one or more patterns or correlations that can be used to predict a next alert for a wearer, to predict sets of conditions under which a wearer is likely to experience an alert event, to generate one or more advance warnings for display via a GUI of the wearer's mobile compute device, etc.

In some embodiments, a wearable monitoring system includes a wearable, hardware-based earpiece, and a mobile app that is compatible with Windows®, iOS®, and Android® compute devices. The earpiece is configured to communicate with a compute device running the mobile app, for example using a power-efficient, lightweight wireless protocol, such as Bluetooth®, BLE®, ZigBee®, Z-Wave®, 6LoWPAN®, Thread®, WiFi-ah® (HaLow®), 2G® (GSM), 3G®, 4G®, LTE® Cat 0®, Cat 1 ®, Cat 3 ®, LTE-M1®, Narrowband IoT® (NB-IoT®), 5G®, NFC®, RFID, SigFox®, LoRaWAN®, Ingenu®, Weightless-N®, Weightless-P®, Weightless-W®, ANT®, ANT+®, DigiMesh®, MiWi®, EnOcean®, Dash?®, or WirelessHART®. The earpiece includes one or more of the following components: one or more light-emitting diodes (LEDs), one or more photosensors/photodetectors, one or more lightweight power-efficient wireless sensors, a speaker, a microphone, one or more air quality monitoring sensors, and one or more body temperature sensors. During operation of the earpiece, the one or more LEDs can transmit light, generated by the one or more LEDS, through a portion of an ear of a wearer of the earpiece, such that the transmitted light is detected by the one or more photosensors/photodetectors, the one or more photosensors/photodetectors disposed on an opposite side of the portion of the ear, as compared with the one or more LEDs. An amount of the light that is absorbed by the ear can be determined/calculated based on the amount of transmitted light detected by the one or more photosensors/photodetectors. A blood oxygen saturation (SpO2) level can then be calculated, based on the amount of light absorbed by the ear, for example using the Beer-Lambert Law ("Beer's Law"). The calculation of the amount of the light absorbed by the ear and/or the calculation of the SpO2 level can be performed by a processor of the earpiece, the mobile app, and/or via a processor of a remote compute device in communication with the earpiece.

In some embodiments, a wearable monitoring system includes a wearable, hardware-based earpiece (wearable oxygen monitor), a charger (e.g., a charging "pod," as shown in FIG. 4), and a mobile app. The wearable oxygen monitor can be in continuous communication via the mobile app, e.g., using one or more wireless antennas or sensors. The charger can be a wireless charger, configured to wirelessly charge the earpiece when the earpiece is at least partially physically received within the charger (and, optionally, when a cover or lid of the charger is closed). The earpiece can be configured to generate and/or send an alarm in response to detecting that an oxygen level of a wearer is lower than a pre-defined threshold value. In addition, the earpiece can be configured to generate and/or send multiple alarms, in response to multiple detections, over time, of an oxygen level of the wearer being lower than the pre-defined threshold value. A frequency of generating and/or sending the alarms can increase in response to detecting that differences between measured/detected/calculated oxygen levels of the wearer and the pre-defined threshold value are getting larger over time (i.e., the measured/detected/calculated oxygen levels of the wearer are decreasing over time, and are all lower than the pre-defined threshold value). Similarly, a frequency of generating and/or sending the alarms can decrease in response to detecting that differences between measured/detected/calculated oxygen levels of the wearer and the pre-defined threshold value are getting smaller over time (i.e., the measured/detected/calculated oxygen levels of the wearer are increasing over time, and are all lower than the pre-defined value). In addition, an intensity or severity of the alarms can increase over time, and/or a type of alarm generated/sent can change over time, in response to detecting that differences between measured/detected/calculated oxygen levels of the wearer and the pre-defined threshold value are getting larger over time. For example, an emitted sound (from the wearable oxygen monitor and/or from the compute device running the mobile app) can get louder, a rate of a flashing light (on the wearable oxygen monitor and/or of the compute device running the mobile app) can increase, a text description of the alarms (e.g., presented to a wearer/user via a GUI of the mobile device running the mobile app) can change from "low" to "moderate," or from "moderate" to high," etc. Similarly, an intensity of the alarms can decrease over time, and/or a type of alarm generated/sent can change over time, in response to detecting that differences between measured/detected/calculated oxygen levels of the wearer and the pre-defined threshold value are getting smaller over time. For example, an emitted sound (from the wearable oxygen monitor and/or from the compute device running the mobile app) can get quieter/softer, a rate of a flashing light (on the wearable oxygen monitor and/or of the compute device running the mobile app) can decrease, a text description of the alarms (e.g., presented to a wearer/user via a GUI of the mobile device running the mobile app) can change from "high" to "moderate," or from "moderate" to low," etc. The alarms can terminate when a most recently measured/detected/calculated oxygen level of the wearer reaches a "normal" level (e.g., at or above the pre-defined threshold value).

Embodiments set forth herein can be used to monitor symptoms of, predict the progression of, and/or as part of a treatment plan for one or more conditions such as pulmonary hypertension (PH), pulmonary arterial hypertension (PAH), idiopathic PAH (IPAH), pulmonary fibrosis, scleroderma, cystic fibrosis, lupus, sickle cell anemia, asthma, chronic obstructive pulmonary disease (COPD), heart disease, and Eisenmenger's Syndrome.

In some embodiments, a wearable oxygen monitor is configured to continuously or intermittently monitor vital signs such as oxygen levels and heart rates, and send data associated with the vital signs (e.g., via the mobile app) for storage in records of a memory or other storage repository, via a mobile app (e.g., implemented using a cloud-based server). In some such instances, when storing the vital signs, the mobile app can also cause the storage of some or all of the following additional information: GPS location of the wearer, altitude of the wearer (e.g., retrieved using a Google application programming interface (API)), an indication of room air quality (e.g., detected by an onboard sensor of the wearable oxygen monitor), environmental temperature, and environmental humidity level.

A wearer or user of the wearable oxygen monitor can subsequently retrieve/download the records (e.g., based on a specified date or date range), for example to show their physician for purposes of diagnosis and/or investigation of causes behind undesirable fluctuations. Alternatively or in addition, the records can automatically be downloaded, for example according to a pre-defined, customizable schedule (e.g., daily, weekly, monthly), and emailed to the wearer and/or other users, medical providers, etc.

In some embodiments, a wearable oxygen monitor is configured to initiate a telephone call to emergency services (e.g., 911) in response to a wearer or user pressing an alert mechanism (e.g., an actuatable button of), or otherwise interacting with an interface of, the wearable oxygen monitor. The button press (or other interaction) can also trigger the activation of an onboard speaker and microphone, to facilitate the telephone call, such that the wearer or user can speak into the microphone and hear the other party on the telephone call via the speaker. This allows the wearer/user to communicate the situation to emergency services and request appropriate help. Optionally, the button press (or other interaction) can also trigger (e.g., concurrently) the generation and wireless sending of an alert via SMS text message to one or more user-defined emergency contact phone numbers (e.g., as defined in the mobile app).

Alternatively or in addition, in some embodiments, a wearable oxygen monitor is configured to generate and send SMS text messages to one or multiple (e.g., 3) emergency contacts pre-defined by a wearer (e.g., as part of a pre-defined emergency plan), in response to the wearer or a user (e.g., a bystander) pressing a button of (or otherwise interacting with an interface of) the wearable oxygen monitor. The SMS text messages can include one or more of the following: an alert message, vital sign data of the wearer, a current GPS location of the wearer, and an indication as to whether emergency services (e.g., 911) have already been called.

In some embodiments, during operation, a wearable oxygen monitor is positioned on a portion of an ear of a wearer, and is in continuous communication (e.g., via one or more wireless antennas, such as Bluetooth®, 4G®, or 5G® antennas) with a mobile app that is concurrently running on a mobile compute device of the wearer. The wearable oxygen monitor. continuously or intermittently over time, detects oxygen levels and heart rates of the wearer, and sends signals to cause display of the detected oxygen levels and heart rates of the wearer via a GUI of the mobile compute device of the wearer. The display of the detected oxygen levels and heart rates can be, for example, in the form of a graph, plot, or chart. The display can be dynamically updated, in real time or substantially in real time, in response to new measurements of oxygen levels and heart rates. When triggered, an alert can be displayed within the GUI, together with or instead of the displayed data.

In some embodiments, the wearable oxygen monitor is an internet-of-things (IoT) device and includes an onboard Long-Term Evolution (LTE) module/chip, for 5G connectivity to other compute devices within the IoT.

Figure 6:
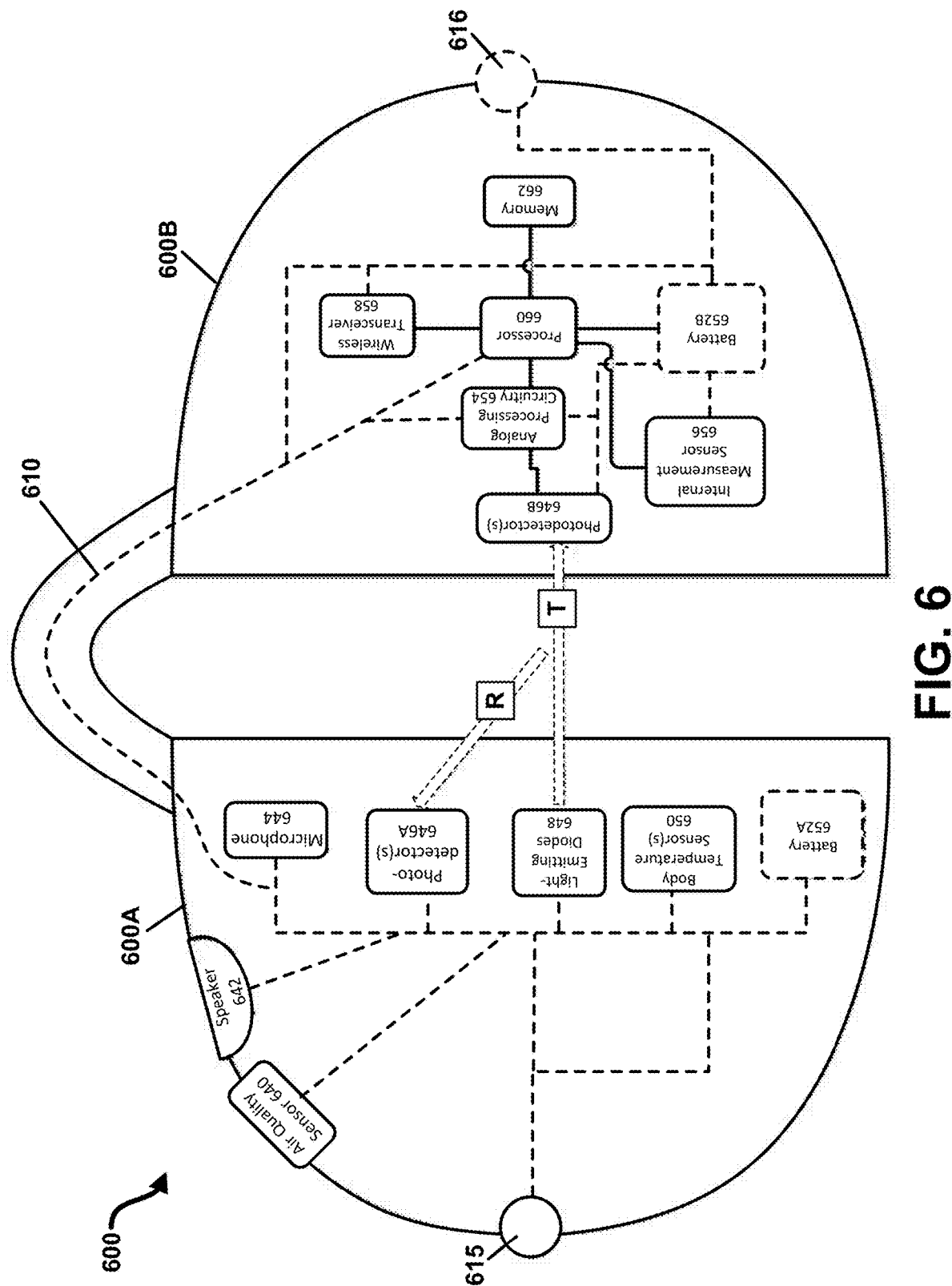
FIG. 6 is a schematic drawing of a wearable oxygen monitor, showing internal components thereof, according to some embodiments.

FIG. 6 is a schematic drawing of a wearable oxygen monitor 600, in cross-section and showing internal components thereof, according to some embodiments. As shown in FIG. 6, and similar to the wearable oxygen monitor 300 of FIG. 3, the wearable oxygen monitor 600 includes a first housing portion 600A (left side—having a substantially hemispherical shape), a second housing portion 600B (right side—having a substantially hemispherical shape), and a connection member 610 mechanically coupled to each of the first housing portion 600A and the second housing portion 600B. The first housing portion 600A includes one or more air quality sensors 640, a speaker 642, an alert mechanism (e.g., an actuatable button) 615, and a microphone 644. In some such embodiments, two or more of the microphone 644, the speaker 642 and the one or more air quality sensors 640 "share" (i.e., are open to external air via) a common opening in an outer shell/wall of the first housing portion 600A, while a remainder of the outer shell/wall of the first housing portion 600A, as well as an entirety of an outer shell/wall of the second housing portion 600B are sealed and waterproof. The one or more air quality sensors 640 can be configured to detect one or more of: biogenic volatile compounds (BVOC), temperature, humidity, carbon monoxide, carbon dioxide, sulfur dioxide, nitrous oxide, particulate matter, ozone and/or other gases. For example, in some embodiments, the one or more air quality sensors 640 are configured to detect temperature, humidity, and one or more BVOCs, and to output a relative "score" of ambient air quality. Alternatively or in addition, the first housing portion 600A and/or the second housing portion 600B can include a Bluetooth® 5.1 Direction Finding capability, for example to identify relative locations of multiple users (e.g., patients within a hospital).

The first housing portion 600A also includes one or more of: one or more photodetectors 646A (e.g., photodiodes), one or more light emitting diodes (LEDs) 648 (e.g., two LEDs), one or more body temperature sensors 650, and an optional battery 652A. The battery 652A can be a rechargeable battery or a non-rechargeable battery. The body temperature sensor(s) 650 can include one or more thermally conductive probes and/or one or more non-contact temperature sensors, such as thermopile infrared (IR) sensors.

The second housing portion 600B includes a processor 660, analog processing circuitry 654, one or more internal measurement sensors 656, one or more wireless transceivers 658, and a memory 662. The one or more internal measurement sensors 656 can include one or more of, for example: an altimeter, gyroscope, accelerometer, GPS sensor, magnetometer, galvanic skin response (GSR) sensor, or a humidity sensor. The processor 660 is operably coupled to each of the analog processing circuitry 654, the one or more internal measurement sensors 656, the one or more wireless transceivers 658, and the memory 662. The second housing portion 600B also includes one or more photodetectors 646B electrically coupled/connected to the analog processing circuitry 654, an alert mechanism (e.g., an actuatable button) 616, and/or an optional battery 652B electrically coupled/ connected to the processor 660. The battery 652B can be a rechargeable battery or a non-rechargeable battery. As shown by the dashed lines in FIG. 6, electrical connections can exist, via the connection member 610 of the wearable oxygen monitor 600, between components in either or both of the first housing portion 600A and the second housing portion 600B (i.e., to some or all of the one or more air quality sensors 640, the speaker 642, the microphone 644, the one or more photodetectors 646A, one or more light emitting diodes (LEDs) 648, one or more body temperature sensors 650, the processor 660, the one or more photodetectors 646B, the analog processing circuitry 654, the one or more internal measurement sensors 656, or the one or more wireless transceivers 658, the alert mechanism 615, the alert mechanism 616, the processor 660) and one or both of the battery 652A and the battery 652B. The alert mechanism 615 and/or the alert mechanism 616 can be electrically connected and/or operably/communicably coupled to one or more of: the battery 652A, battery 652B, the processor 660, the analog processing circuitry 654, or the wireless transceiver 658.

The processor 660 can be configured to control (e.g., turn on and off) one more of: the one or more air quality sensors 640, the speaker 642, the microphone 644, the one or more photodetectors 646A, the one or more photodetectors 646B, the one or more light-emitting diodes 648, the one or more body temperature sensors 650, the battery 652A, the battery 652B, the analog processing circuitry 654, the internal measurement sensor 656, and/or the wireless transceiver 658. Alternatively or in addition, the processor can be configured to receive signals, measurements and/or data from one or more of: the one or more air quality sensors 640, the microphone 644, the one or more photodetectors 646A, the one or more photodetectors 646B, or the one or more body temperature sensors 650. The memory 662 can store instructions to cause the processor 660 to perform analytics or to calculate one or more metrics based on the measurements and/or data detected/generated by sensors and other components onboard the wearable oxygen monitor 600. For example, the memory 662 can store instructions to cause the processor 660 to predict or assess whether an alert event (e.g., a detected occurrence of hypoxia) was caused due to a physical reason or due to an environmental factor. The processor 660 can store measurements and/or data in the memory 662, and can retrieve data stored in the memory, e.g., for inclusion in signals transmitted, via the wireless transceiver 658, to a mobile app and/or to one or more remote compute devices, optionally for presentation via a GUI of the one or more remote compute devices. In addition to the measurements and/or data generated on sensors and other components onboard the wearable oxygen monitor 600, the memory 662 can also store processor-executable instructions (software) to cause the processor to perform actions, as well as one or more user-customizable emergency plans, as discussed herein.

In some embodiments, the memory 662 stores instructions to cause the processor 660 to detect that the alert mechanism 615 and/or the alert mechanism 616 has been interacted with (e.g., pressed) by a wearer (i.e., a manual alert), and, in response to detecting that the alert mechanism 615 and/or the alert mechanism 616 has been interacted with, generate and send (via the wireless transceiver) a message to one or multiple emergency contacts stored in the memory 662 (e.g., as part of an emergency plan stored therein). The memory 662 can also store instructions to cause the processor 660, in response to detecting that the alert mechanism 615 and/or the alert mechanism 616 has been interacted with, to: initiate a telephone call to emergency services (911), activate the speaker 642, activate the microphone 644, emit a sound to indicate an alarm, emit a light to indicate an alarm, generate and send (via the wireless transceiver) an alert message to the mobile app for presentation to a user via a GUI of the user's compute device, and cause storage to memory of an alert record including a date stamp, a time stamp, and measurement data collected from components of the wearable oxygen monitor 600 (e.g., the air quality sensor 640, the photodetectors 646A, 646B, the body temperature sensor(s) 650, the internal measurement sensor(s) 656) at the time of the alert.

Alternatively or in addition, the memory 662 can store instructions to cause the processor 660 to compare a predetermined threshold stored in the memory 662 with one or more measurements collected by one or more components of the wearable oxygen monitor 600. When the processor determines that the one or more measurements are undesirably below or undesirably above the predetermined threshold, the processor can detect that an alarm condition is present. The memory 662 can also store instructions to cause the processor 660, in response to detecting the alarm condition, generate and send (via the wireless transceiver) a message to one or multiple emergency contacts stored in the memory 662 (e.g., as part of an emergency plan stored therein). The memory 662 can also store instructions to cause the processor 660, in response to detecting the alarm condition, to: initiate a telephone call to emergency services (911), activate the speaker 642, activate the microphone 644, emit a sound to indicate an alarm, emit a light to indicate an alarm, generate and send (via the wireless transceiver) an alert message to the mobile app for presentation to a user via a GUI of the user's compute device, and cause storage to memory of an alert record including a date stamp, a time stamp, and measurement data collected from components of the wearable oxygen monitor 600 (e.g., the air quality sensor 640, the photodetectors 646A, 646B, the body temperature sensor(s) 650, the internal measurement sensor(s) 656) at the time of the alert.

In some implementations, the first housing portion 600A of the wearable oxygen monitor 600 includes the battery 652A, while the second housing portion 600B of the wearable oxygen monitor 600 does not include the battery 652B. In such implementations, the single battery 652A can supply power to components in each of the first housing portion 600A and the second housing portion 600B (i.e., to some or all of the one or more air quality sensors 640, the speaker 642, the microphone 644, the one or more photodetectors 646A, one or more light emitting diodes (LEDs) 648, one or more body temperature sensors 650, the processor 660, the analog processing circuitry 654, the one or more internal measurement sensors 656, or the one or more wireless transceivers 658). In other implementations, the second housing portion 600B of the wearable oxygen monitor 600 includes the battery 652B, while the first housing portion 600A of the wearable oxygen monitor 600 does not include the battery 652A. In such implementations, the single battery 652B can supply power to components in each of the first housing portion 600A and the second housing portion 600B (i.e., to some or all of the one or more air quality sensors 640, the speaker 642, the microphone 644, the one or more photodetectors 646A, one or more light emitting diodes (LEDs) 648, one or more body temperature sensors 650, the processor 660, the analog processing circuitry 654, the one or more internal measurement sensors 656, or the one or more wireless transceivers 658). In still other implementations, the first housing portion 600A of the wearable oxygen monitor 600 includes the battery 652A, and the second housing portion 600B of the wearable oxygen monitor 600 includes the battery 652B, for example such that the battery 652A supplies electrical power to components in the first housing portion 600A of the wearable oxygen monitor 600 (i.e., the one or more air quality sensors 640, the speaker 642, the microphone 644, the one or more photodetectors 646A, one or more light emitting diodes (LEDs) 648, and/or the one or more body temperature sensors 650), and the battery 652B supplies electrical power to components in the second housing portion 600B of the wearable oxygen monitor 600 (i.e., the processor 660, the analog processing circuitry 654, the one or more internal measurement sensors 656, and/or the one or more wireless transceivers 658).

Alternatively or in addition, in some implementations, the first housing portion 600A of the wearable oxygen monitor 600 includes the one or more photodetectors 646A, while the second housing portion 600B of the wearable oxygen monitor 600 does not include the one or more photodetectors 646B. In other implementations, the second housing portion 600B of the wearable oxygen monitor 600 includes the one or more photodetectors 646B, while the first housing portion 600A of the wearable oxygen monitor 600 does not include the one or more photodetectors 646A. In still other implementations, the first housing portion 600A of the wearable oxygen monitor 600 includes the one or more photodetectors 646A, and the second housing portion 600B of the wearable oxygen monitor 600 includes the one or more photodetectors 646B.

To commence use of the wearable oxygen monitor 600, a wearer positions the wearable oxygen monitor 600 about a portion of the wearer's ear (e.g., the upper ear, such as the helix, scapha, or pinna of the ear), in a wear configuration. In a first example wear configuration, the first housing portion 600A of the wearable oxygen monitor 600 is in contact with or adjacent to an anterior or front surface of the ear, and the second housing portion 600B of the wearable oxygen monitor 600 is in contact with or adjacent to a posterior or back/rear surface of the ear. In a second example wear configuration, the second housing portion 600B of the wearable oxygen monitor 600 is in contact with or adjacent to an anterior or front surface of the ear, and the first housing portion 600A of the wearable oxygen monitor 600 is in contact with or adjacent to a posterior or back/rear surface of the ear. Stated another way, when the wearable oxygen monitor 600 is worn, the first housing portion 600A and the second housing portion 600B are positioned on opposite sides of the wearer's ear.

In some embodiments, the first housing portion 600A of the wearable oxygen monitor 600 includes the one or more photodetectors 646A and the second housing portion 600B of the wearable oxygen monitor 600 includes the one or more photodetectors 646B. During use and operation of the wearable oxygen monitor 600, the one or more light-emitting diodes 648 can emit light along the direction of the arrow labelled "T" in FIG. 6, such that at least a portion of the emitted light transmits or propagates through the portion of the wearer's ear and is detected at the photodetector(s) 646B (referred to herein as "transmissive sensing") of the second housing portion 600B. As also shown in FIG. 6, at least a portion of the emitted light may be reflected (e.g., along the direction of the arrow labelled "R" in FIG. 6) and detected at the photodetector(s) 646A (referred to herein as "reflective sensing") of the first housing portion 600A. In some such embodiments, the one or more light-emitting diodes 648 includes two light-emitting diodes 648—one for transmissive sensing and one for reflective sensing. A first light-emitting diode 648 from the two light-emitting diodes 648 can be configured to emit light having a first wavelength, and a second light-emitting diode 648 from the two light-emitting diodes 648 can be configured to emit light having a second wavelength different from the first wavelength.

Although shown and described, with respect to FIG. 6, to be in particular portions (first housing portion 600A or second housing portion 600B) of the wearable oxygen monitor 600, any component or combination of components of the wearable oxygen monitor 600 (i.e., air quality sensor 340, speaker 642, microphone 644, photodetector(s) 646A, LED(s) 648, body temperature sensor(s) 650, battery 652A, battery 652B, photodetector(s) 646B, analog processing circuitry 654, internal measurement sensor(s) 656, processor 660, wireless transceiver 658 and/or memory 662) can alternatively be positioned in the first housing portion 600A, the second housing portion 600B, or both, depending upon the particular embodiment.

In some embodiments, the memory 662 stores instructions to cause the processor 660 to calculate one or more scores based on readings/measurements from one or more of the air quality sensor 640, the photodetector(s) 646A, 646B, the body temperature sensor(s) 650, or the internal measurement sensor(s) 656. The memory 662 can also store instructions to cause the processor 660 to perform an alert-related action in response to determining that one or more of the calculated scores is below a predefined minimum threshold value or above a predefined maximum threshold value. The alert-related action can include one or more of: initiating a telephone call to emergency services (911), activating the speaker 642, activating the microphone 644, emitting a sound to indicate an alarm, emitting a light to indicate an alarm, generating and sending (via the wireless transceiver) an alert message to the mobile app for presentation to a user via a GUI of the user's compute device, and causing storage to memory of an alert record including a date stamp, a time stamp, and measurement data collected from components of the wearable oxygen monitor 600 (e.g., the air quality sensor 640, the photodetectors 646A, 646B, the body temperature sensor(s) 650, the internal measurement sensor(s) 656) at the time of the alert.

Alternatively or in addition, the memory 662 can store instructions to cause the processor 660 to compare one or more scores, ranges or thresholds, stored in the memory 662, to one or more readings/measurements from one or more of the air quality sensor 640, the photodetector(s) 646A, 646B, the body temperature sensor(s) 650, or the internal measurement sensor(s) 656, to determine whether an out-of-tolerance condition is present. The memory 662 can also store instructions to cause the processor 660 to perform an alert-related action in response to determining that an out-of-tolerance condition is present. The alert-related action can include one or more of: initiating a telephone call to emergency services (911), activating the speaker 642, activating the microphone 644, emitting a sound to indicate an alarm, emitting a light to indicate an alarm, generating and sending (via the wireless transceiver) an alert message to the mobile app for presentation to a user via a GUI of the user's compute device, and causing storage to memory of an alert record including a date stamp, a time stamp, and measurement data collected from components of the wearable oxygen monitor 600 (e.g., the air quality sensor 640, the photodetectors 646A, 646B, the body temperature sensor(s) 650, the internal measurement sensor(s) 656) at the time of the alert.

Figure 7:
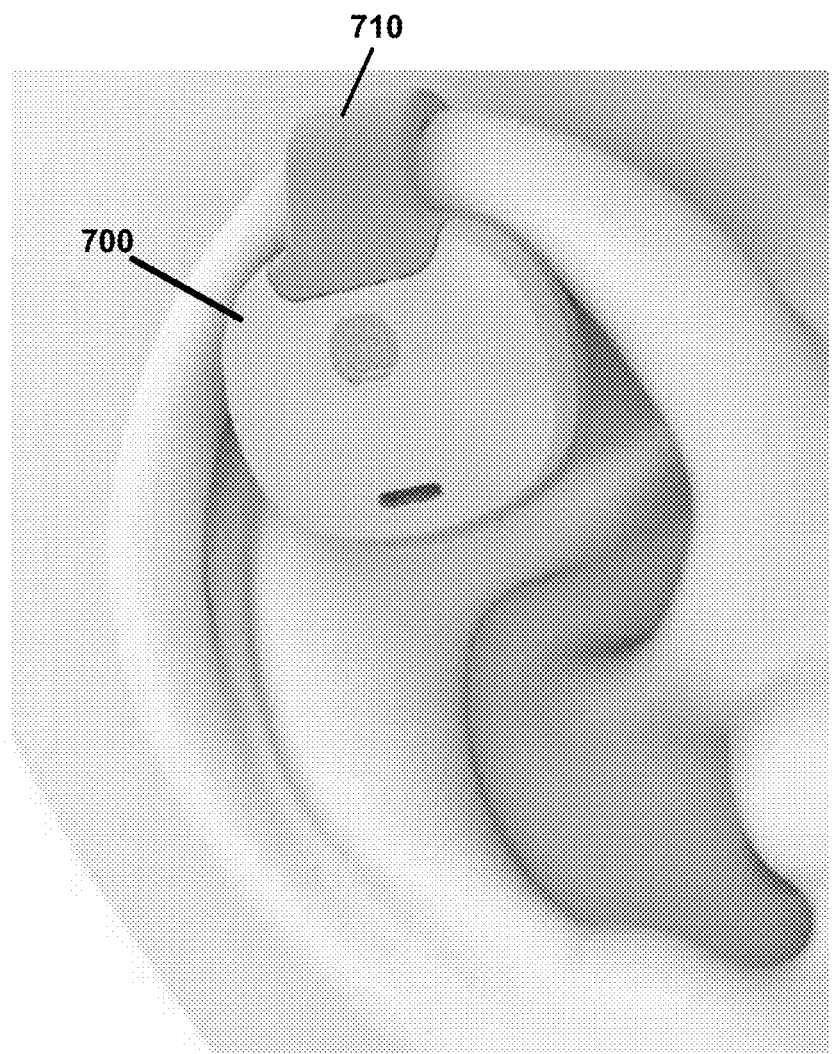
FIG. 7 is a rendering of a wearable oxygen monitor, configured to be worn about an upper portion of an ear of a user, according to an embodiment.

FIG. 7 is a rendering of a wearable oxygen monitor 700, configured to be worn about an upper portion of an ear of a user, according to an embodiment. As shown in FIG. 7, the wearable oxygen monitor 700, when worn by a wearer, can be positioned about the helix, scapha, pinna, or earlobe of the ear, with a connection member 710 of the wearable oxygen monitor 700 (joining first and second housing portions of the wearable oxygen monitor) traversing an upper edge of the ear and mechanically supporting the wearable oxygen monitor 700 in place.

FIGS. 8A-8B are renderings of views of a wearable oxygen monitor 800 in a portable charging case 850, according to an embodiment. As shown in FIG. 8A, the portable charging case 850 includes a charging port 852 for electrical connection to a power supply. The portable charging case 850 includes multiple pockets, receptacles, chambers or depressions defined therein, into which the wearable oxygen monitor 800 can be at least partially received and positioned/ stabilized. When the wearable oxygen monitor 800 is at least partially received within the pockets or depressions, the wearable oxygen monitor 800 can be wirelessly charged by the portable charging case 850, when the portable charging case 850 is connected to the power supply via the charging port 852, and optionally when a rechargeable battery (not shown) within the portable charging case 850 has been at least partially charged and is no longer connected to the power supply via the charging port 852.

Figure 8D:
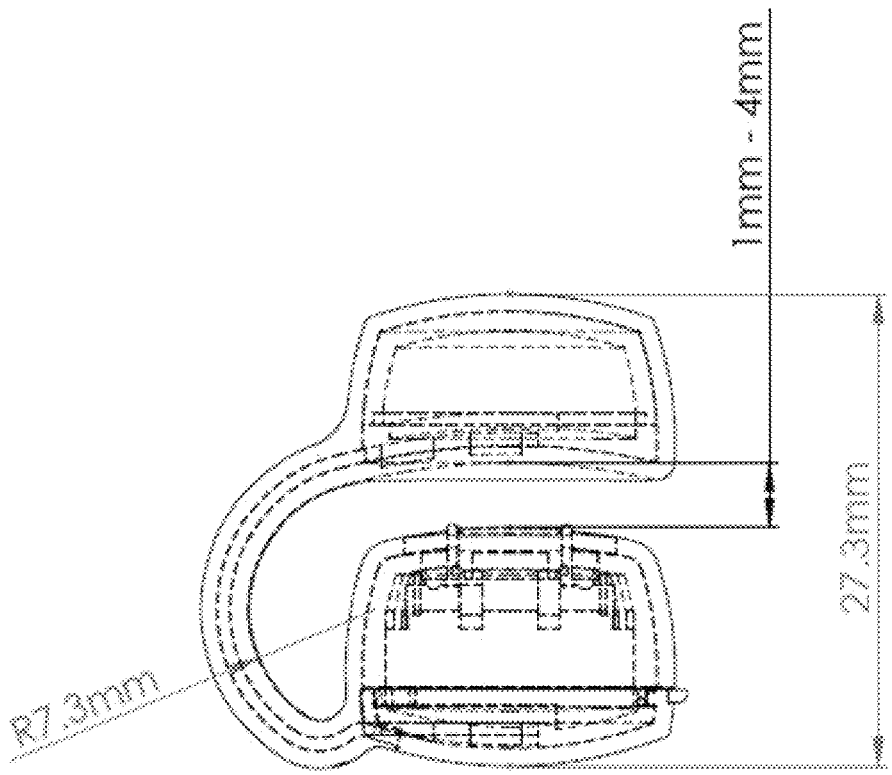
FIGS. 8C-8D are renderings of views of a wearable oxygen monitor, with example dimensions shown, according to an embodiment.
Figure 8C:
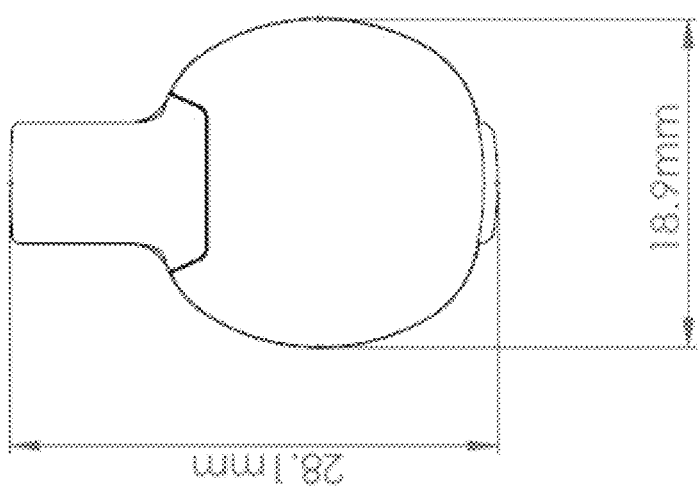

FIGS. 8C-8D are renderings of views of a wearable oxygen monitor (such as the wearable oxygen monitor 800 of FIGS. 8A-8B), with example dimensions shown, according to an embodiment. As shown in FIG. 8C, the wearable oxygen monitor has a maximum width of 18.9 mm and a maximum height of 28.1 mm. As shown in FIG. 8D, the wearable oxygen monitor has a gap of between 1 mm and 4 mm, a maximum depth of 27.3 mm, and a radius of curvature of the connecting member of 7.3 mm.

Figure 9:
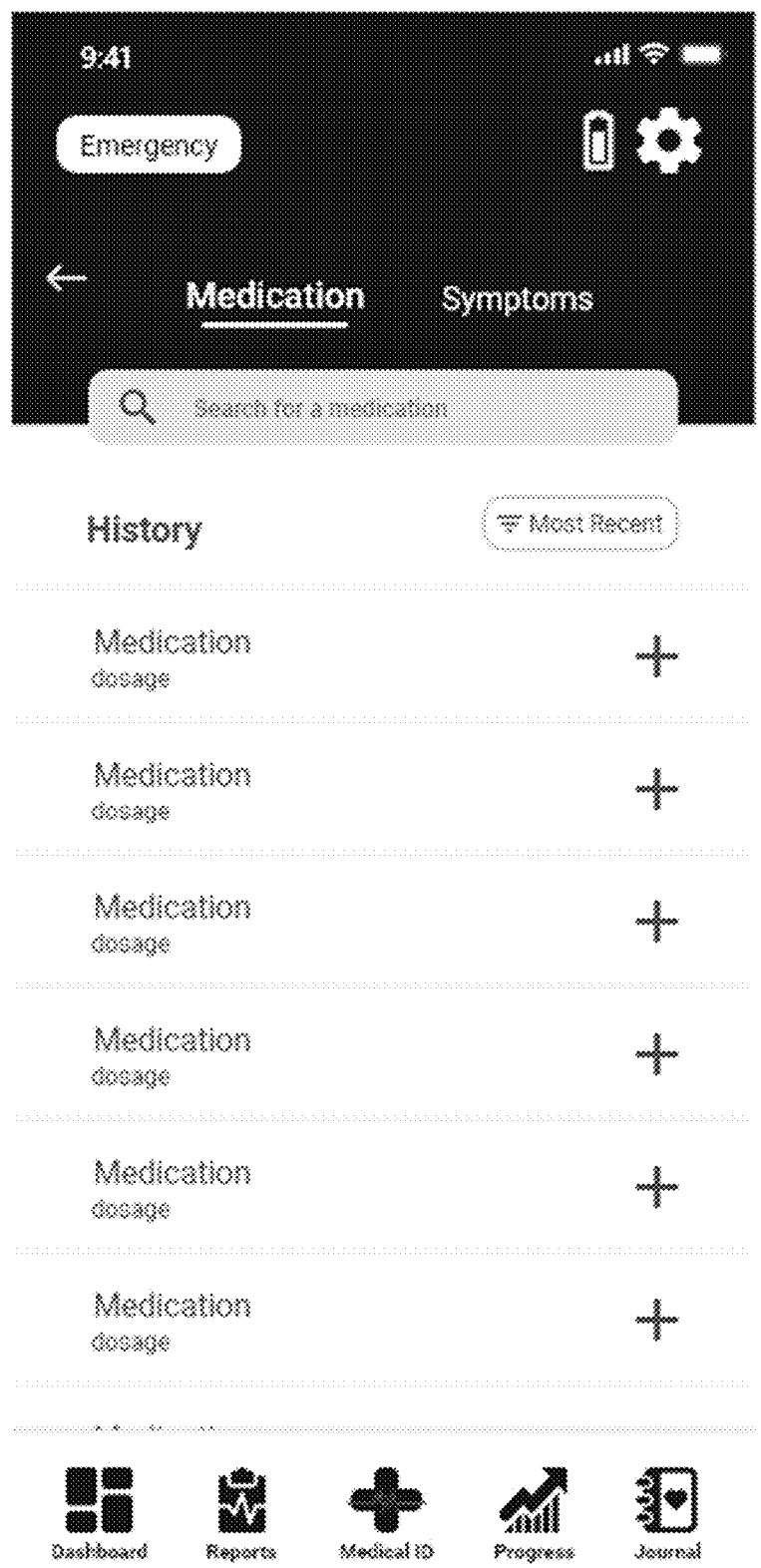

FIGS. 9-45 are wireframes of user interface screens (for GUI display) of a mobile app (e.g., running on a mobile compute device) that interacts with a wearable oxygen monitor, according to some embodiments. As shown in FIG. 9, a user of the mobile app (optionally also a wearer of an associated wearable oxygen monitor, as shown and described herein) can create a user profile in the mobile app. The creation of a user profile can include specifying one or more medications that the user is currently taking or has taken in the past. The user interface can include a search bar in which the user can enter search criteria pertaining to one or more medications, and by pressing ENTER, can cause a search to be executed for matches to the search criteria. The results identified via the search can then be displayed for selection via the user interface. The user can "add" medications to their user profile by clicking on the "+" symbol next to the relevant medication(s). Also shown in FIG. 9 are the available/navigable screens: "Dashboard," "Reports," "Medical ID," "Progress" and "Journal."

Figure 10:
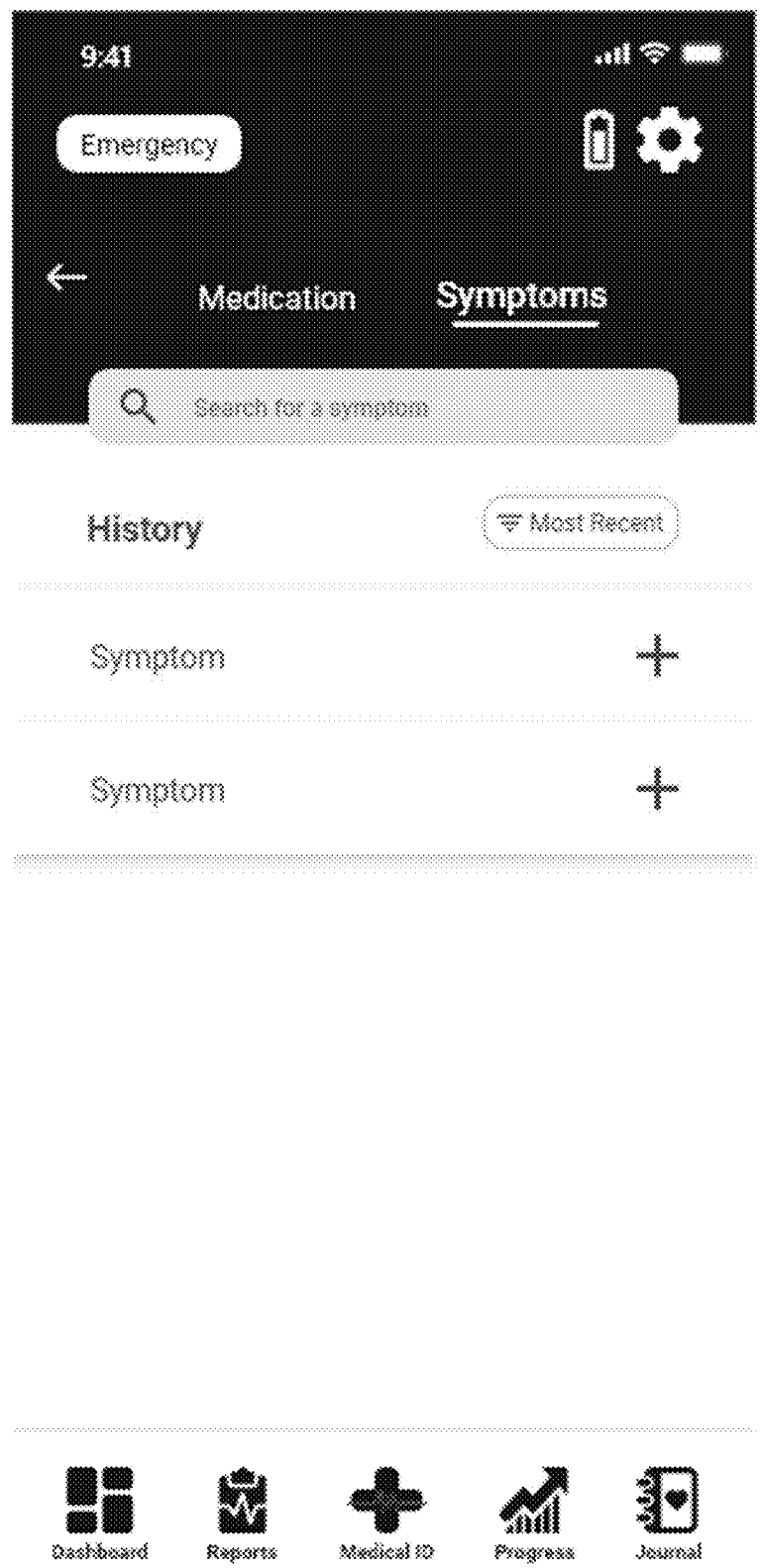
Figure 11:
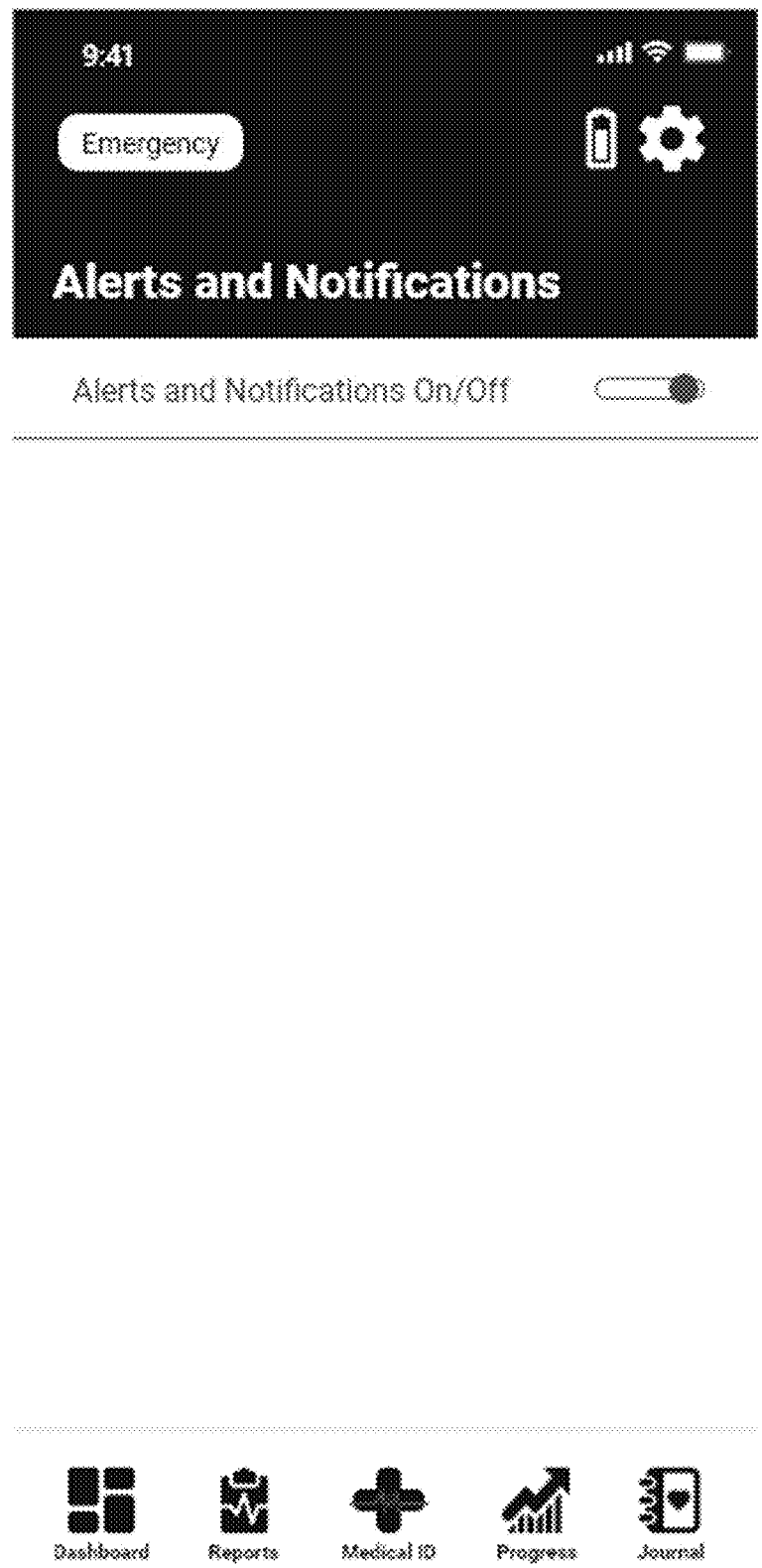
Figure 12:
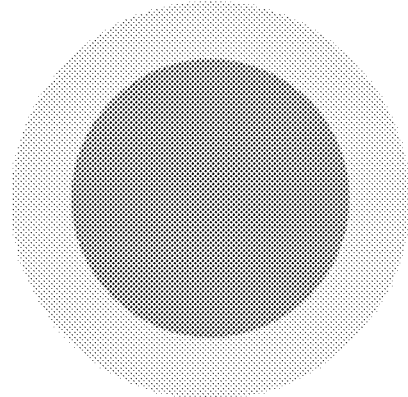
Figure 12:
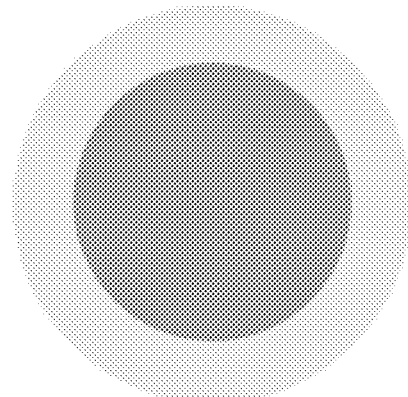
Figure 12:
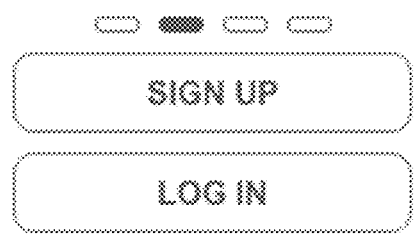
Figure 13:
Figure 14:
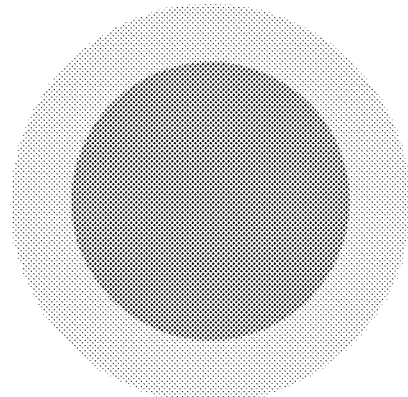
Figure 14:
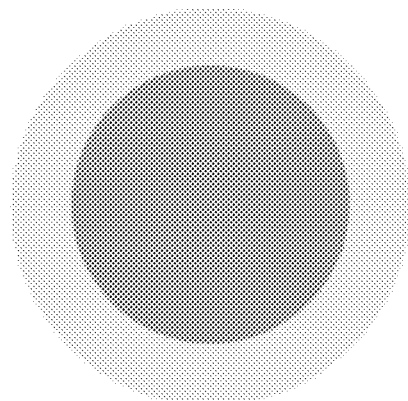
Figure 14:
Figure 15:
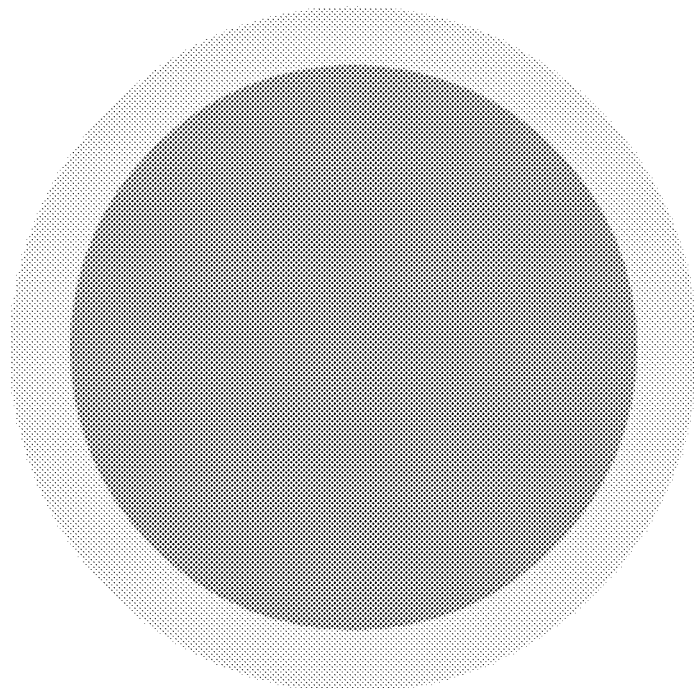
Figure 16:
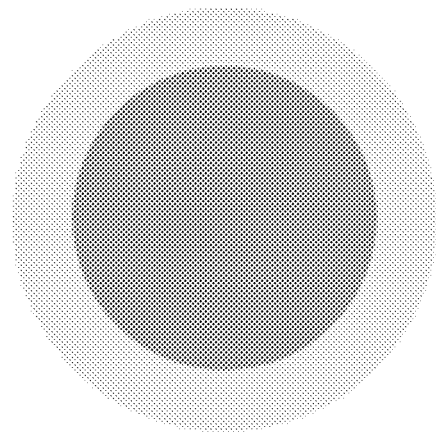

FIG. 10 shows that the creation of a user profile can also include specifying one or more symptoms that the user is currently experiencing or has experienced in the past. The use interface can include a search bar in which the user can enter search criteria pertaining to one or more symptoms, and by pressing ENTER, can cause a search to be executed for matches to the search criteria. The results identified via the search can then be displayed for selection via the user interface. The user can "add" symptoms to their user profile by clicking on the "+" symbol next to the relevant symptom(s). The user interface also includes an "Emergency" button that the user can select to trigger one or more alerts to be generated and/or sent. For example, selecting the "Emergency" button, similar to pressing the alert mechanism of the wearable oxygen monitor described herein, can trigger one or more of the following: generating and sending a message to one or multiple emergency contacts (e.g., stored as part of an emergency plan), initiating a telephone call to emergency services (911), activating speakerphone on the mobile compute device, emitting a sound to indicate an alarm, emitting a light (e.g., of a predetermined color and/or in a predetermined pattern) to indicate an alarm, displaying an alert message via the user interface, and causing storage, in memory, of an alert record including a date stamp, a time stamp, and measurement data collected from components of the wearable oxygen monitor. FIG. 11 shows an Alerts and Notifications user interface, via which the user can turn alerts and notifications on or off, using a slider.

Figure 17:
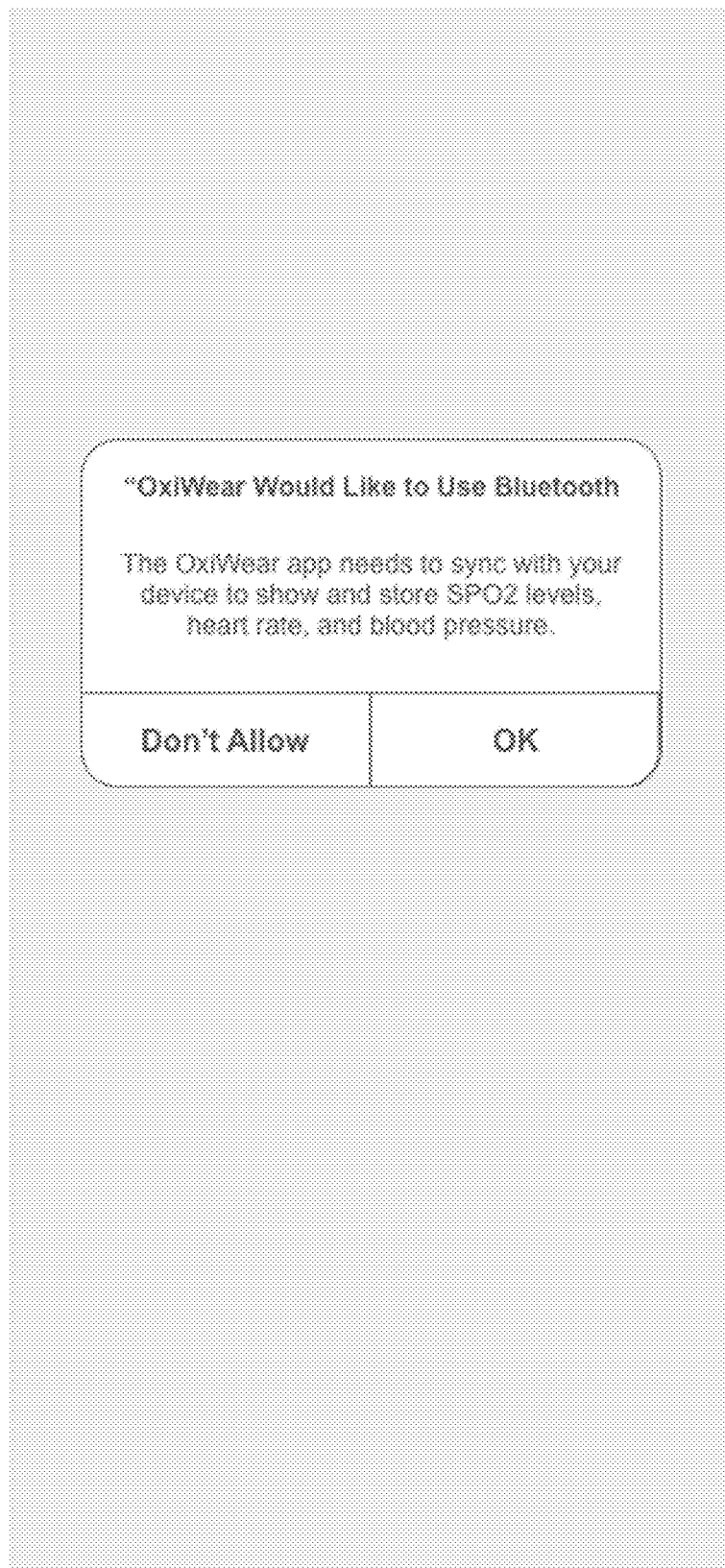
Figure 18:
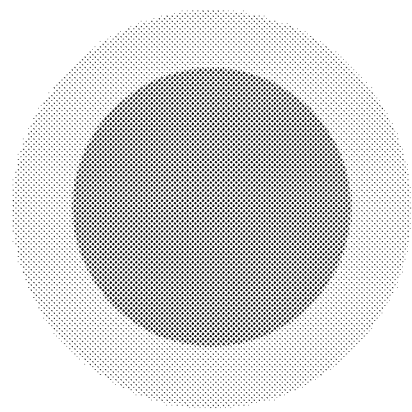
Figure 19:
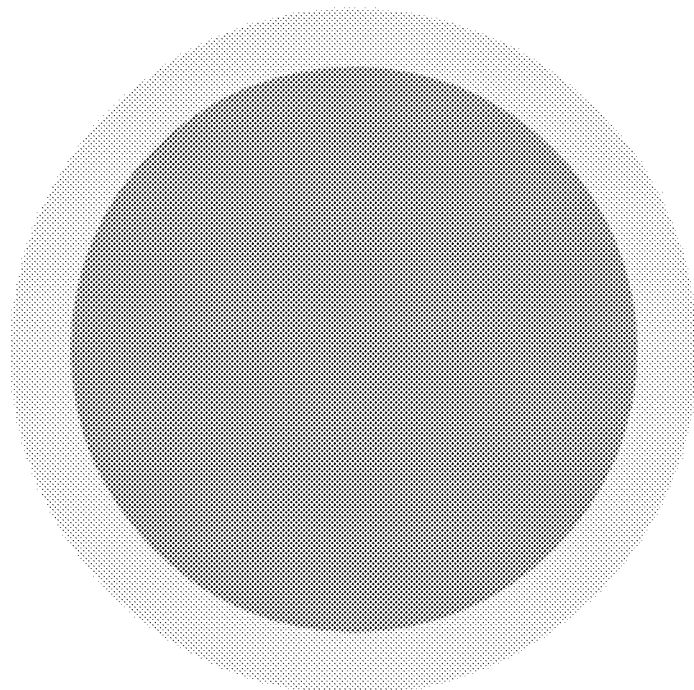
Figure 19:
Figure 20:
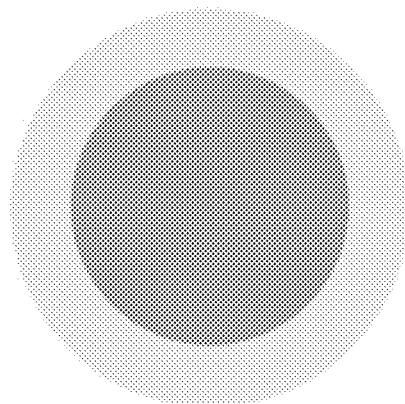
Figure 22:
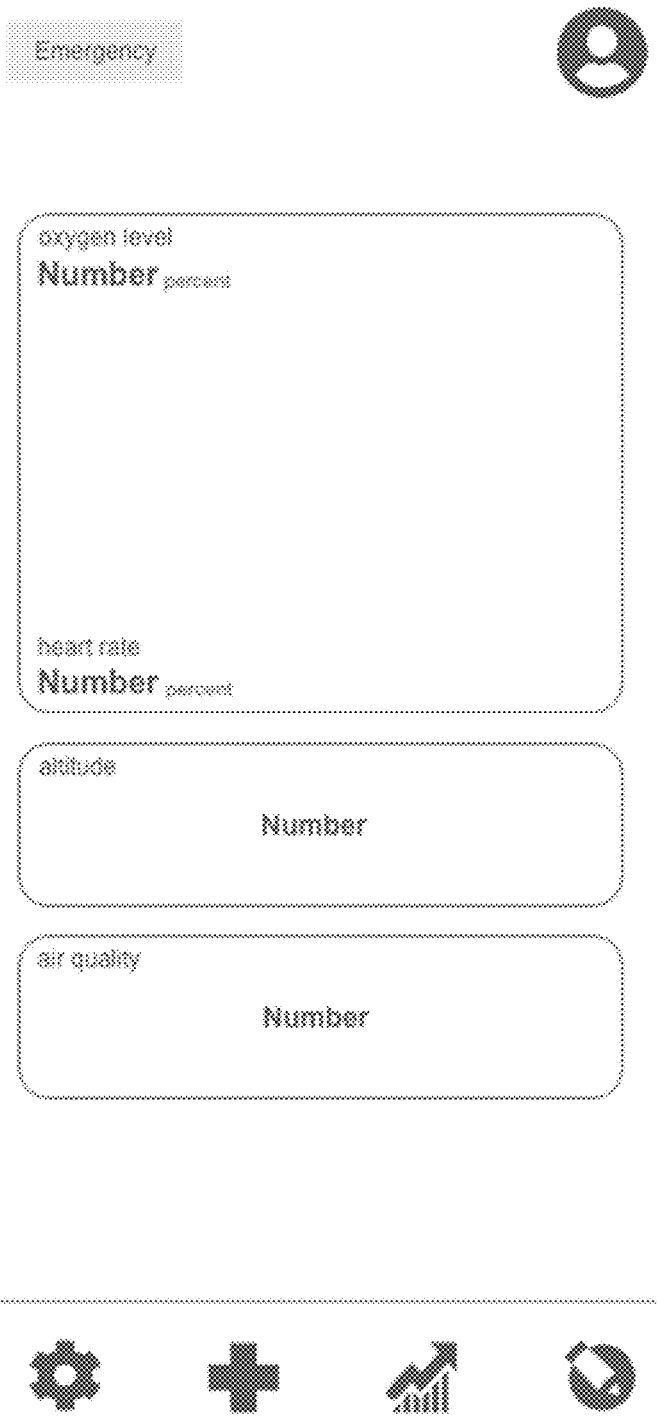
Figure 23:
Figure 23:
Figure 23:
Figure 23:
Figure 23:
Figure 23:
Figure 23:
Figure 23:
Figure 23:
Figure 23:
Figure 23:
Figure 24:
Figure 24:
Figure 24:
Figure 24:
Figure 24:
Figure 25:
Figure 25:
Figure 25:
Figure 25:
Figure 25:
Figure 26:
Figure 26:
Figure 26:
Figure 26:
Figure 26:
Figure 27:
Figure 27:
Figure 29:
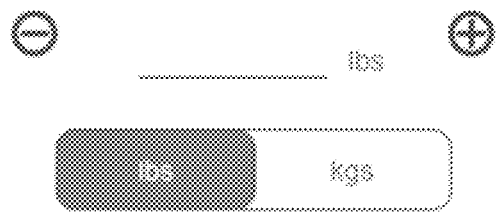
Figure 31:
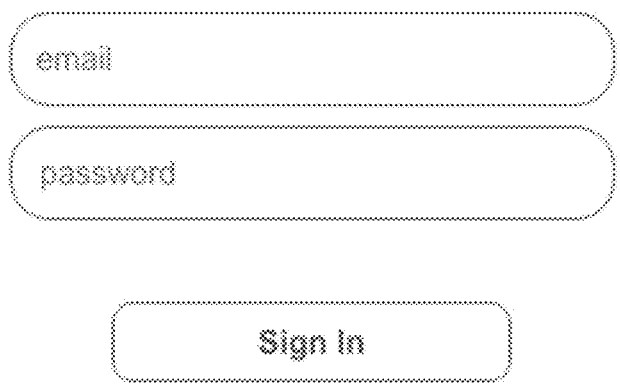

FIGS. 12-16 show welcome screens describing the mobile app's functionality, and via which a user can sign up for services (see FIG. 13), log in, set up, and personalize the mobile app. The mobile app can be personalized, for example, to include a representation of one or more safe blood oxygen saturation (SpO2) thresholds, such that a warning or alert is generated when the wearer's SpO2 is detected, by the wearable oxygen monitor, as being too low. FIG. 17 shows a synchronization request, in which the mobile app requests the user's input ("OK") to authorize the mobile app to establish a Bluetooth® connection and synchronize ("sync") the mobile app, via the Bluetooth® connection, with the wearable oxygen monitor. The user interface appearance, during synchronization, is shown in FIG. 18. FIG. 19 shows the login screen, and FIG. 20 shows an option for the user to "Get Started," for example after a first login event by the user. FIGS. 21-33 show user interfaces (e.g., presented sequentially) of a questionnaire requesting input from the user as to: whether they are from the U.S., what the emergency threshold values for oxygen level, heart rate, altitude and air quality should be, settings (alerts and notifications, location services, unit preferences, language preference, app sync, and other personalization), profile data (name, age, gender, weight, pulmonary hypertension (PH) class (e.g., pulmonary arterial hypertension (PAH), pulmonary hypertension owing to left heart disease, chronic obstructive pulmonary disease, chronic thromboembolic pulmonary hypertension (CTEPH), or pulmonary hypertension with unclear multifactorial mechanisms), safe threshold, medication(s), and allergies/reactions), journal personalization, emergency information (emergency contacts, doctor's notes, notes for EMS), gender, birth month and year, weight, whether or not they have a cardiovascular disease, and whether or not they have pulmonary hypertension (and, if so, what World Health Organization (WHO) classification).

Figure 34:
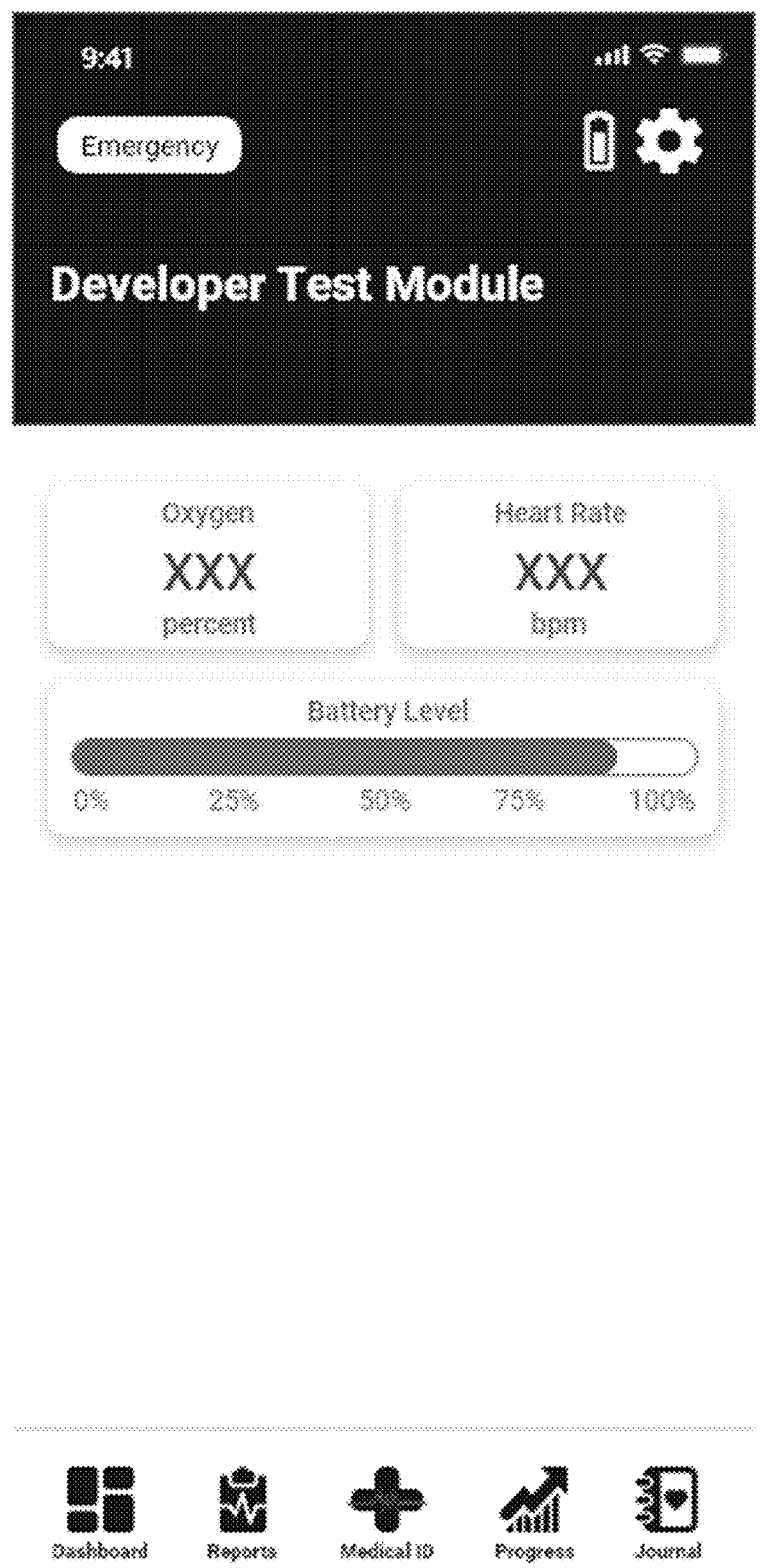
Figure 35:
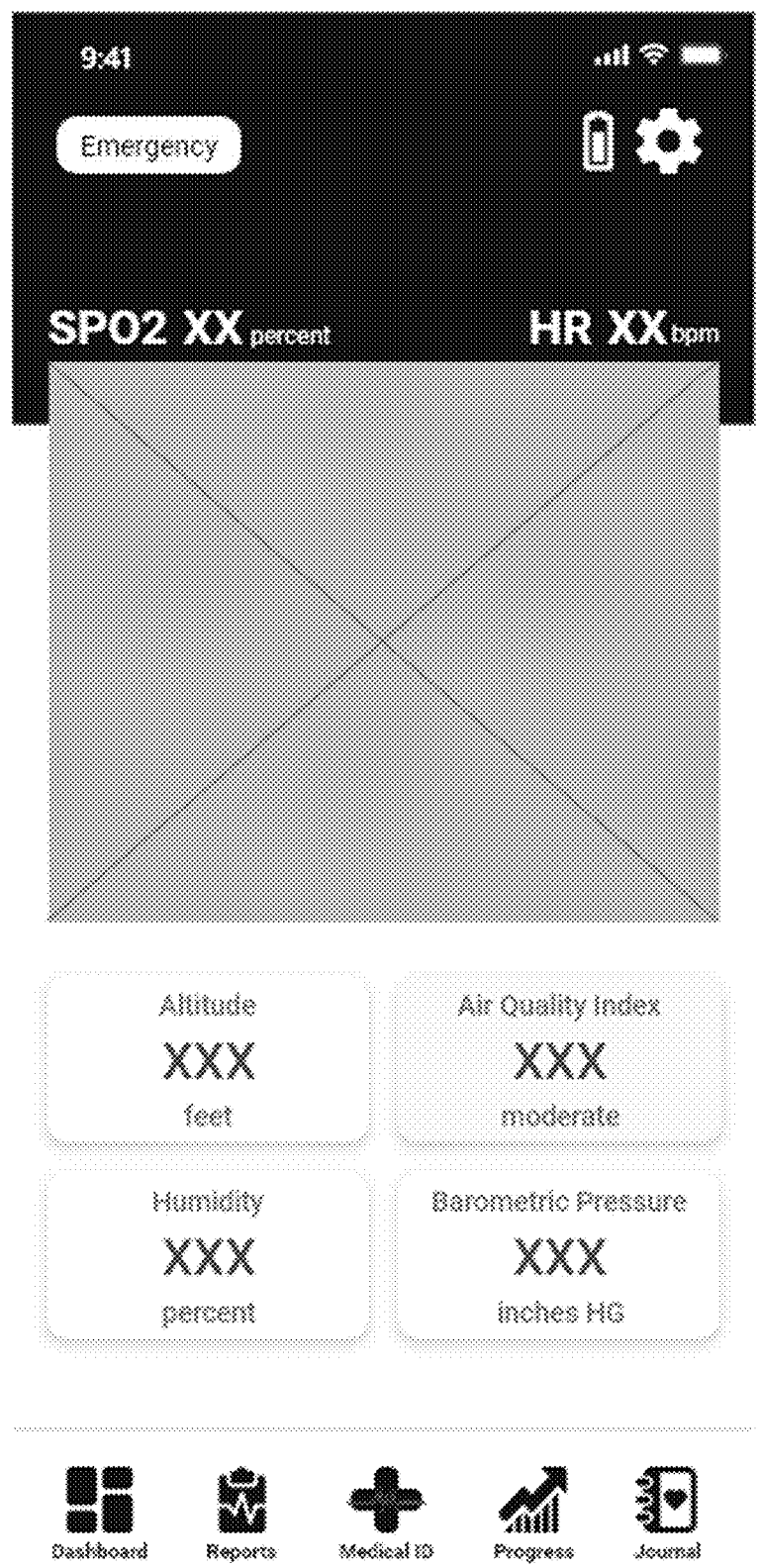
Figure 36:
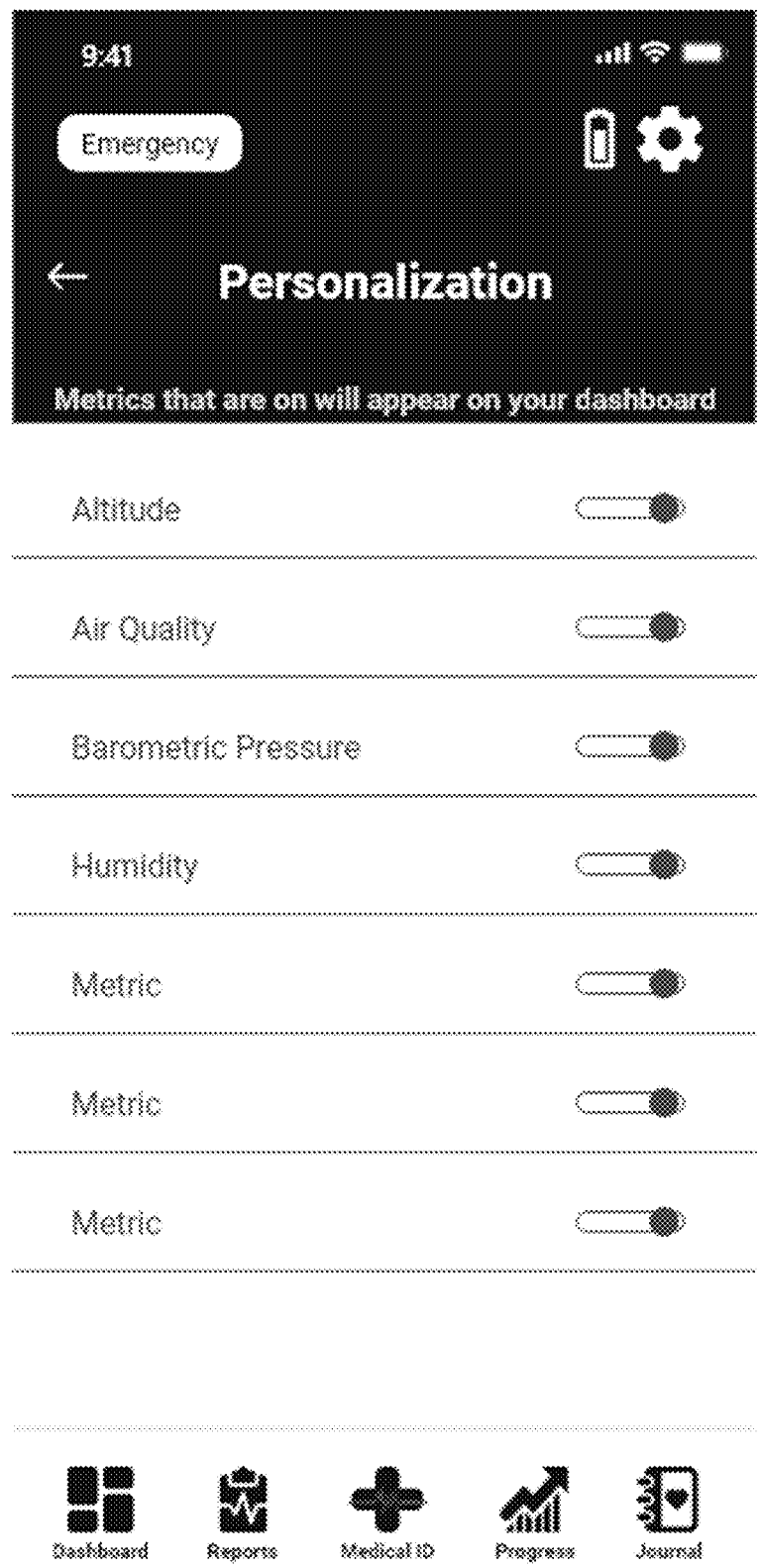
Figure 37:
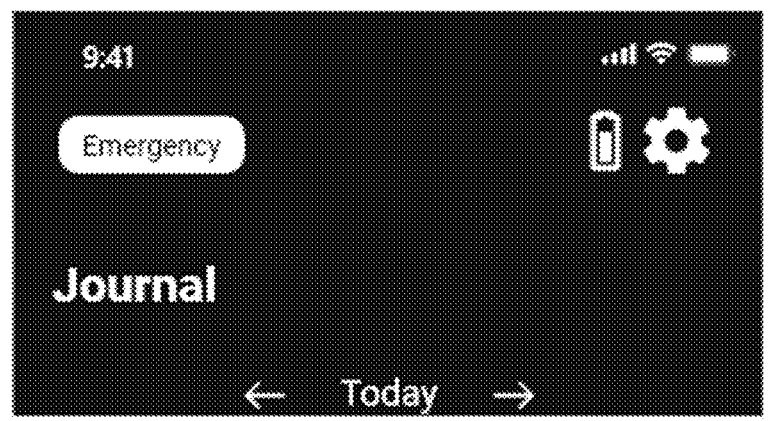
Figure 37:
Figure 37:
Figure 37:
Figure 37:
Figure 37:
Figure 37:
Figure 37:
Figure 37:
Figure 37:
Figure 37:
Figure 38:
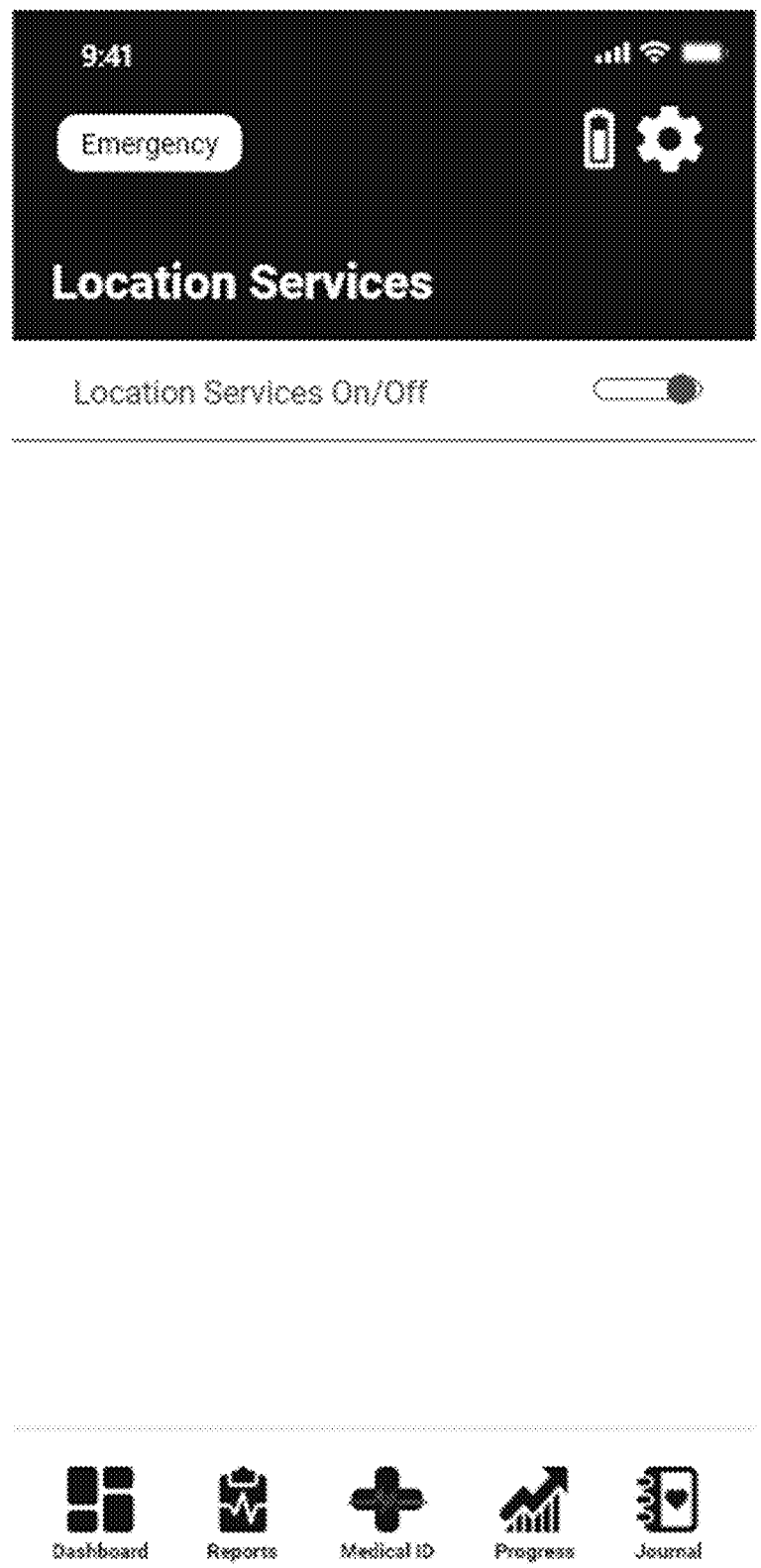
Figure 39:
Figure 40:
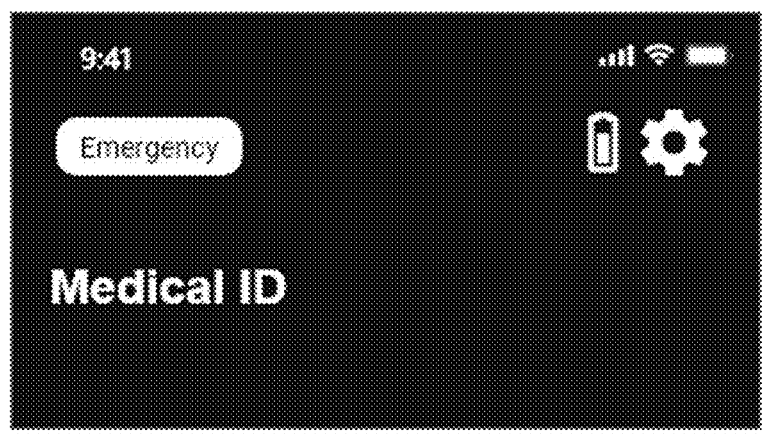
Figure 40:
Figure 41:
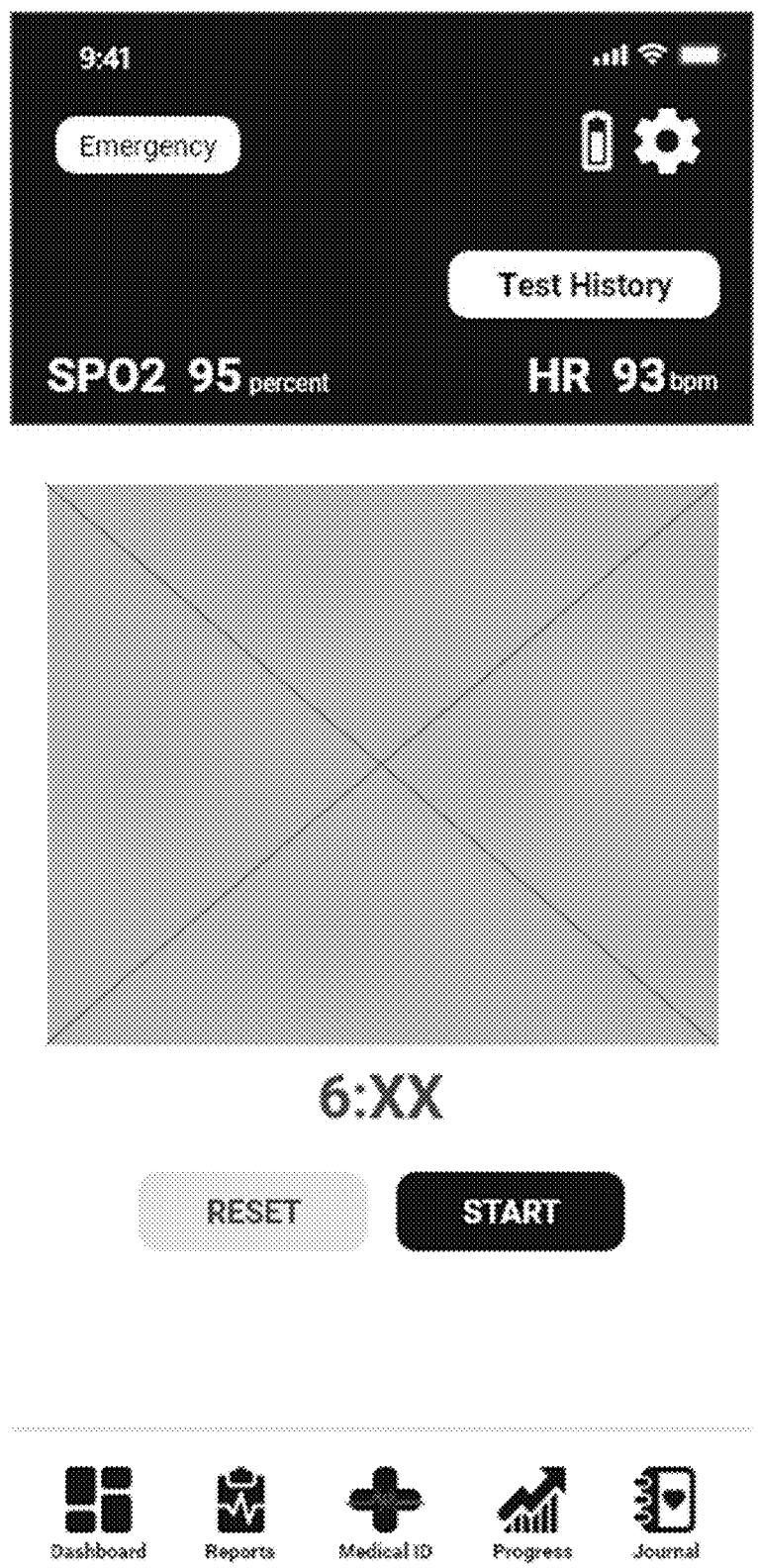
Figure 42:
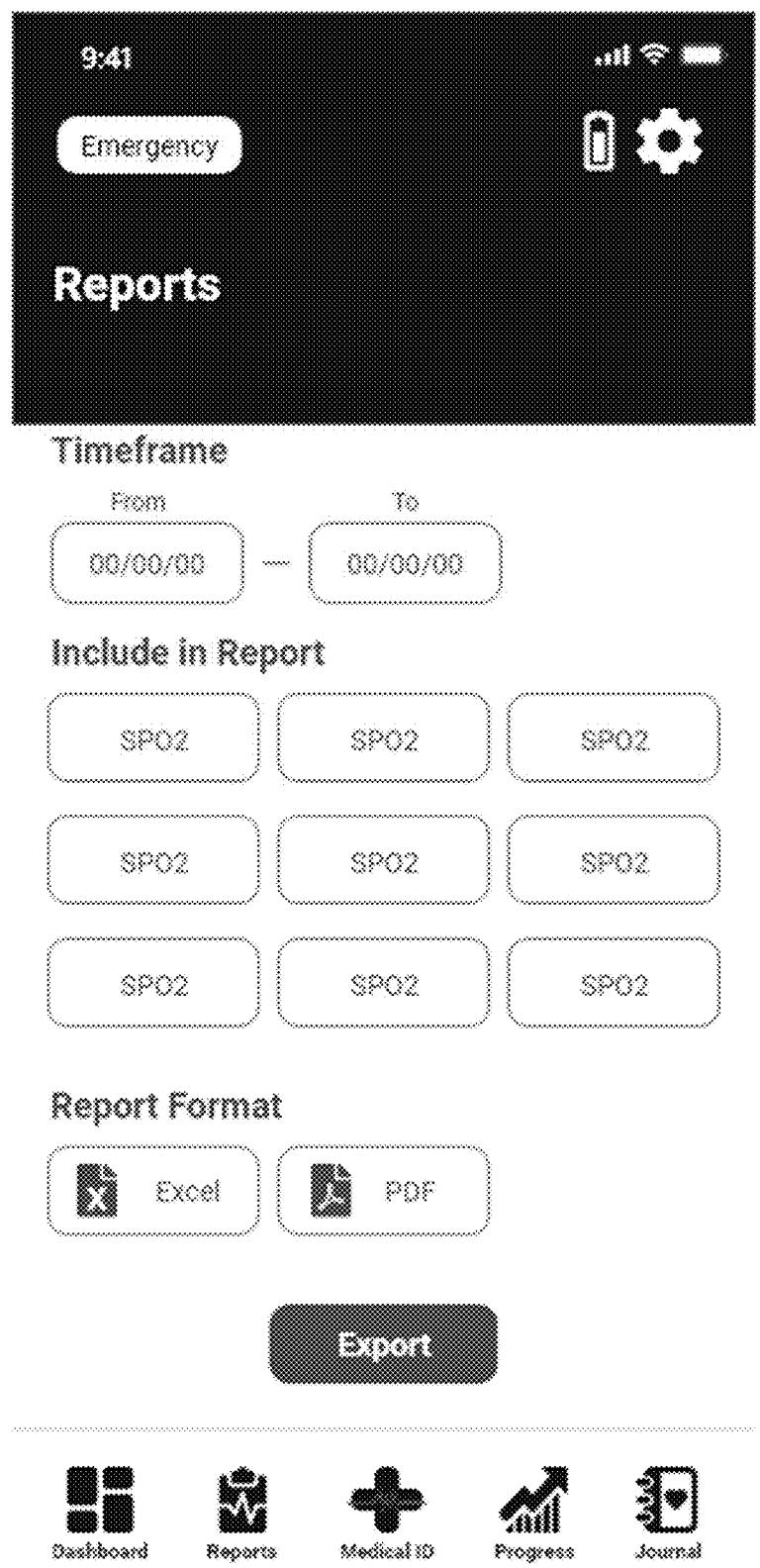
Figure 43:
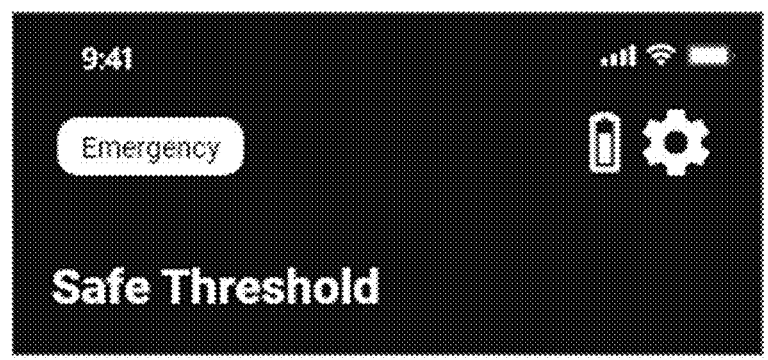
Figure 43:
Figure 43:
Figure 43:
Figure 43:
Figure 43:
Figure 43:
Figure 44:
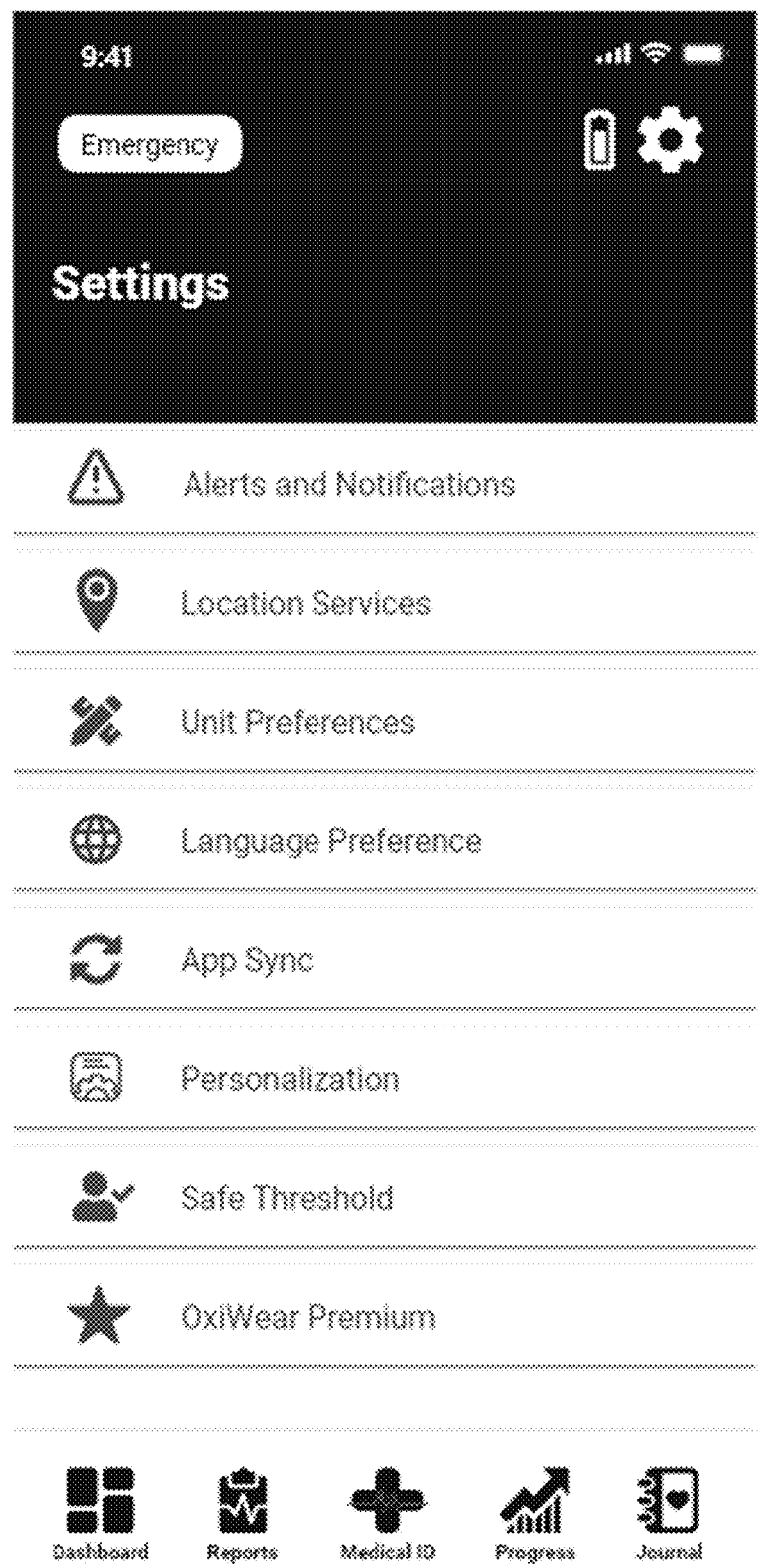
Figure 45:
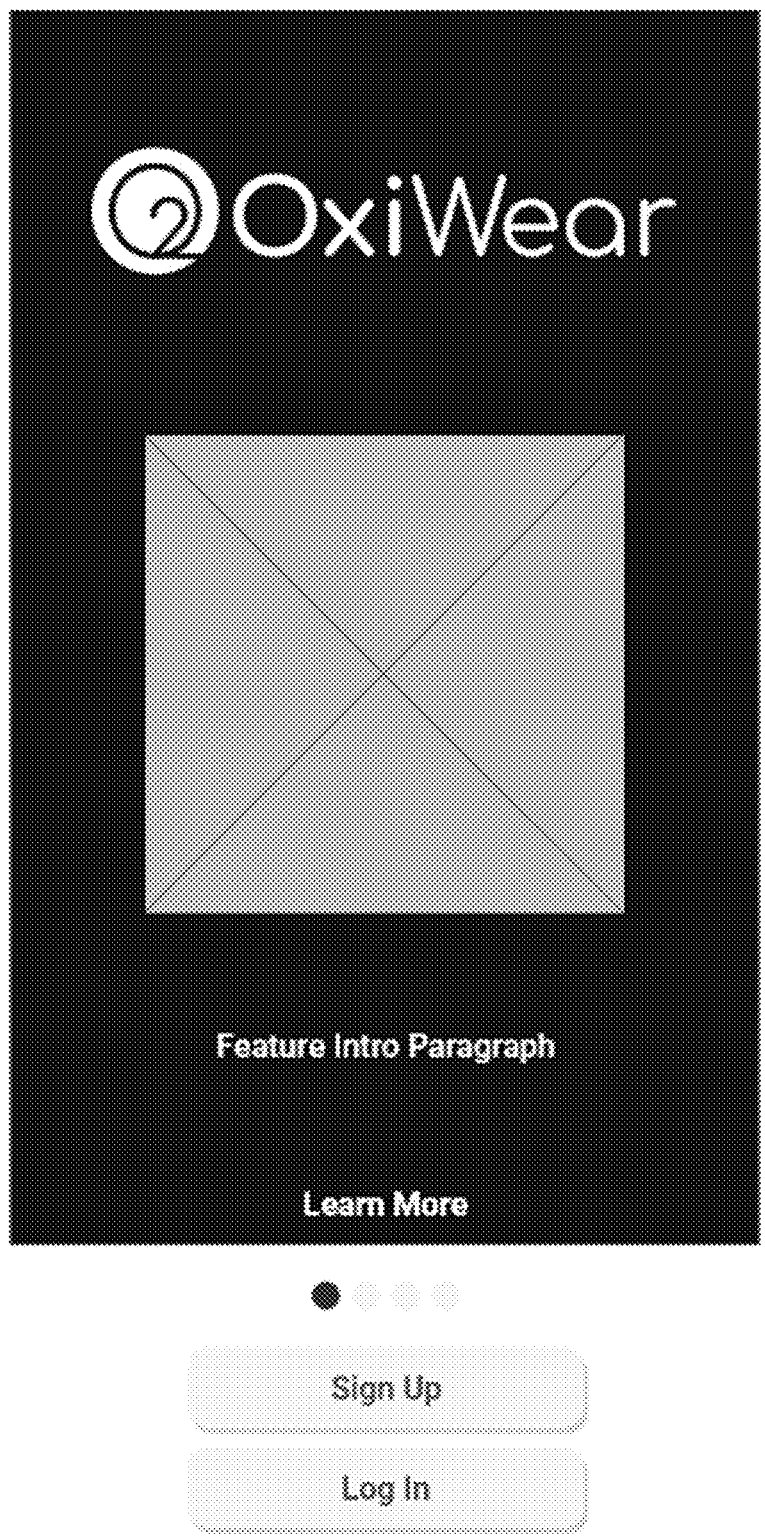

FIG. 34 shows a developer test module screen with a battery level indication and current oxygen level (percentage) and heart rate (beats per minute, BPM) readings. FIG. 35 shows current blood oxygen saturation level (percentage) and heart rate (beats per minute, BPM) readings, along with current altitude (feet), humidity (percent), air quality index (e.g., good, moderate, poor), and barometric pressure (inches mercury (Hg)). FIG. 36 shows a user interface via which the user can select which metrics they wish to have appear on their dashboard page. FIG. 37 shows an example journal entry for the current day, with date, time, SpO2, heart rate, altitude, air quality index, barometric pressure, and humidity values (e.g., average values, high values, etc.), together with medications taken on the current day (if any), symptoms experienced on the current day (if any), and notes entered by the user (if any). FIG. 38 shows a Location Services user interface, via which the user can turn location services (e.g., GPS location) on or off, using a slider. FIG. 39 shows a user interface accessible, for example, to users having a premium account, or providing the user with option to sign up for a premium account. The premium account can provide the user access to features such as predictive analysis, detailed report generation, and the presentation of weekly and monthly vital signs via the mobile app dashboard. FIG. 40 is a user interface showing a populated Medical ID tab. FIG. 41 is a user interface showing current oxygen level (percentage) and heart rate (BPM) readings, along with a resettable timer. FIG. 42 is a user interface showing user-selectable options for report generation, including timeframe, vital signs of interest, and report format (e.g., Microsoft® Excel® or Adobe® PDF®). FIG. 43 shows a Safe Threshold user interface, via which the user can set a threshold percentage SpO2 value, using a slider, and select "Done" when complete. FIG. 44 is a user interface showing Settings after Safe Thresholds have been set and a premium account has been established (as contrasted with the Settings shown in FIG. 23, which do not include a Safe Threshold or OxiWear Premium line item). FIG. 45 is a user interface showing an example landing screen that may display when the mobile app is first launched/opened (i.e., the first screen that a first-time user will see, and via which he/she can register for an account).

In some embodiments, an apparatus for monitoring a blood oxygen saturation level of a wearer of the apparatus includes a processor, a memory operably coupled to the processor, a first housing portion, a second housing portion, and a connection member. The first housing portion includes at least one light-emitting diode (LED), and the second housing portion includes a photodetector. The connection member is mechanically coupled to each of the first housing portion and the second housing portion. The apparatus can be sized and shaped to be worn about a portion of an ear of a wearer of the apparatus. During operation, the at least one LED emits light in a direction toward the photodetector. A portion of the emitted light passes through the portion of the ear prior to arriving at the photodetector. The photodetector detects the portion of the emitted light (e.g., by generating and detecting a voltage signal or a current signal in response to the portion of the emitted light impinging on its surface), and the memory stores instructions to cause the processor to calculate a blood oxygen saturation level of the wearer based on the detected signal.

In some embodiments, the photodetector is a first photodetector, the portion of the emitted light is a first portion of the emitted light, and the first housing portion also includes a second photodetector configured to detect a second, reflected, portion of the emitted light. The memory also stores instructions to cause the processor to calculate the blood oxygen saturation level of the wearer based on the detection of the first portion of the emitted light and the detection of the second portion of the emitted light.

In some embodiments, the apparatus also includes at least one of a microphone or a speaker operatively coupled to the processor, and the memory also stores instructions to cause the processor to activate the at least one of the microphone or the speaker in response to detecting an alarm condition.

In some embodiments, the apparatus also includes a wireless transceiver, operatively coupled to the processor and configured to communicate with a mobile software application. The memory also stores instructions to cause the processor to send signals representing measurement data to the mobile software application via the wireless transceiver.

In some embodiments, the memory also stores instructions to cause the processor to send signals, according to a predetermined schedule, to a mobile software application, the signals representing measurement data.

In some embodiments, the apparatus also includes at least one sensor operatively coupled to the processor, the at least one sensor including at least one of: a body temperature sensor, an air quality sensor, a humidity sensor, an altimeter, or a barometric pressure sensor, The memory also stores instructions to cause the processor to store, in the memory, data collected by the at least one sensor.

In some embodiments, the apparatus also includes at least one sensor operatively coupled to the processor, the at least one sensor including at least one of: a body temperature sensor, an air quality sensor, a humidity sensor, an altimeter, or a barometric pressure sensor, The memory also stores instructions to cause the processor to send signals, according to a predetermined schedule, to a mobile software application, the signals representing data collected by the at least one sensor.

In some embodiments, an apparatus includes a processor, a memory operably coupled to the processor, at least one light-emitting diode operatively coupled to the processor, a photodetector operatively coupled to the processor, and multiple sensors operatively coupled to the processor. The apparatus can be sized and shaped to mechanically attach to a portion of an ear of a wearer of the apparatus. The at least one light-emitting diode is configured, during operation, to emit light in a direction toward the photodetector, a portion of the emitted light passing through the portion of the ear prior to arriving at the photodetector. The photodetector is configured to detect the portion of the emitted light. The memory stores instructions to cause the processor to calculate a blood oxygen saturation level of the wearer based on the detected portion of the emitted light, and to store, in memory, a representation of the calculated blood oxygen saturation level and at least one measurement collected by the plurality of sensors.

In some embodiments, the plurality of sensors includes at least one of: a body temperature sensor, an air quality sensor, a humidity sensor, an altimeter, or a barometric pressure sensor.

In some embodiments, the photodetector is a first photodetector, the portion of the emitted light is a first portion of the emitted light, and the apparatus also includes a second photodetector configured to detect a second, reflected, portion of the emitted light, The memory also stores instructions to cause the processor to calculate the blood oxygen saturation level of the wearer based on the detection of the first portion of the emitted light and the detection of the second portion of the emitted light.

In some embodiments, the apparatus also includes at least one of a microphone or a speaker, operatively coupled to the processor, The memory also stores instructions to cause the processor to activate the at least one of the microphone or the speaker in response to detecting an alarm condition.

In some embodiments, the apparatus also includes a wireless transceiver, operatively coupled to the processor and configured to communicate with a mobile software application, The memory also stores instructions to cause the processor to send signals representing measurement data to the mobile software application via the wireless transceiver.

In some embodiments, the memory also stores instructions to cause the processor to send signals, according to a predetermined schedule, to a mobile software application, the signals representing the at least one measurement collected by the plurality of sensors.

In some embodiments, the apparatus also includes an alert mechanism operatively coupled to the processor, the memory further storing instructions to cause the processor to generate and send a signal representing an alert in response to detecting a user interaction with the alert mechanism.

In some embodiments, an apparatus includes a processor, a memory operably coupled to the processor, a light-emitting diode, and a photodetector. The apparatus is sized and shaped to mechanically attach to a portion of an ear of a wearer of the apparatus. The memory stores instructions to cause the processor to calculate a blood oxygen saturation level of the wearer based on a detected portion of an emitted light at the photodetector, the signal resulting from an emission of the at least one light-emitting diode. The memory also stores instructions to cause the processor to compare the calculated blood oxygen saturation level to a predetermined threshold blood oxygen saturation level, and to generate an alert in response to detecting that the calculated blood oxygen saturation level is lower than the predetermined threshold blood oxygen saturation level.

In some embodiments, the memory also stores instructions to cause the processor to perform at least one of the following, in response to detecting that the calculated blood oxygen saturation level is lower than the predetermined threshold blood oxygen saturation level: (1) initiating a communication with an emergency services entity; (2) sending one of a short message service (SMS) text or email message to at least one emergency contact, based on emergency contact information stored in the memory; (3) causing a sound to be emitted from the apparatus; (4) causing the apparatus to vibrate, using a haptic feedback device; (5) sending a signal to a mobile software application to cause display, at a compute device of the wearer, of a representation of the alert; (6) sending a signal to a mobile software application to cause the compute device of the wearer to vibrate; or (7) sending a signal to a mobile software application to cause the compute device of the wearer to emit a sound.

In some embodiments, the instructions to cause the processor to compare the calculated blood oxygen saturation level to a predetermined threshold blood oxygen saturation level include instructions to perform multiple such comparisons over time, according to a predefined schedule.

In some embodiments, the photodetector is a first photodetector, the portion of the emitted light is a first portion of the emitted light, and the apparatus also includes a second photodetector configured to detect a second, reflected, portion of the emitted light, The memory also stores instructions to cause the processor to calculate the blood oxygen saturation level of the wearer based on the detection of the first portion of the emitted light and the detection of the second portion of the emitted light.

In some embodiments, the apparatus also includes at least one of a microphone or a speaker operatively coupled to the processor. The memory also stores instructions to cause the processor to activate the at least one of the microphone or the speaker in response to detecting that the calculated blood oxygen saturation level is lower than the predetermined threshold blood oxygen saturation level.

In some embodiments, the memory also stores instructions to cause the processor to send signals, according to a predefined schedule, to a mobile software application, the signals representing measurement data.

Wearable Oxygen Monitor Applications—COVID-19

The novel coronavirus (Coronavirus disease 2019 (COVID-19) is an infectious disease, caused by severe acute respiratory syndrome coronavirus 2 (SARS-CoV-2), that disrupts functions of many organ systems and has resulted in hundreds of thousands of deaths to date. COVID-19 impacts the respiratory system, with effects ranging from mild upper respiratory symptoms to pneumonia and acute respiratory distress syndrome. One potential COVID-19-induced symptom is silent hypoxia, in which a patient experiences below-average (or "low") tissue and blood oxygen saturation, yet does not exhibit breathlessness. Although the mechanisms through which silent hypoxia emerges are unclear, the phenomenon warrants significant clinical and public health attention. Silent hypoxia presents at least two problems, with regard to public health: 1) Infected individuals may progress to more severe disease states yet may be unaware that they are COVID-positive, and 2) Infected, silently hypoxic patients may serve as vectors to infect those around them ("asymptomatic spread"). For hypoxic patients, continuous blood oxygen saturation monitoring is important. As such, there is a desire for smart, portable, and wearable devices that provide real-time SpO2 monitoring and alarm users when their SpO2 levels drop below acceptable levels.

One or more embodiments of the wearable oxygen monitor set forth herein can perform robust blood oxygen saturation level monitoring, for a variety of applications, including: the identification of silently hypoxic patients, helping alert healthcare providers to patients at risk of serious disease progression, augmenting existing COVID-19 diagnostic platforms such as nasopharyngeal swabs, preventing the spread of COVID-19, assisting healthcare providers in the coordination of care, and monitoring one or more of a variety of health conditions detailed below. Normal blood oxygen saturation levels are approximately 95 percent. When a patient exhibits blood oxygen saturation below this threshold, the patient's organ systems, particularly the brain, may receive inadequate oxygen supply, which could lead to confusion or lethargy. If the oxygen level drops below 80 percent, there is risk of serious damage to vital organs, potentially leading to death.

COVID-19 has been reported to induce silent hypoxia in patients. According to Dr. Richard Levitan, an emergency doctor at New York City's Bellevue Hospital, those suffering from COVID-induced silent hypoxia do not experience difficulty breathing until the day they arrive at the hospital. It follows that a subset of COVID-19 patients is entirely asymptomatic despite having COVID-induced hypoxia for a period of time, suggesting that the silently hypoxic patients could spread the infection to others and also progress to more serious COVID-19 stages.

A continuous blood oxygen saturation monitor is desirable, to protect vulnerable members of the population and to facilitate the detection of low blood oxygen saturation as early as possible. High-sensitivity monitoring can help to ensure that patients receive medical assistance before their condition deteriorates, thereby improving patient outcomes and helping the healthcare system manage the current burden of the pandemic.

COVID-19 Symptoms and Risk Factors

Fever, designated by the Centers for Disease Control and Prevention as body temperature above 100.4 degrees Celsius, is the symptom most commonly associated with COVID-19 among the public. However, clinical observational analysis at Northwell Health, the largest provider system in New York, indicates that only 30.7% of patients diagnosed with COVID-19 were febrile upon clinical presentation. The weak correlation between fever and infection suggests that the presentation of COVID-19 is enormously variable, and that providers should screen patients for multiple parameters when assessing the presence or severity of infection.

Although the relationship between febrility and infection is unclear, clinical studies demarcate specific risk factors that can make patient populations more vulnerable to serious infection. According to observations of COVID-19 positive patients at Northwell Health, 56.6% had a history of hypertension, 41.7% had a history of obesity, and 33.8% were diabetic. The strong correlations between chronic pre-existing conditions and COVID-19 hospitalization underscore the desirability of robust monitoring, particularly of high-risk populations.

Clinical observations also suggest the desirability of prognostic markers for COVID-19, which could help ensure that patients are treated earlier and more aggressively, and help in preventing progression to mechanical ventilation, which is associated with significantly higher mortality. In connection with planned reopenings of workplaces and schools, some entities are planning to use thermal scanners to flag febrile individuals. Afebrile individuals, however, may act as vectors for the spread of infection despite not exhibiting this benchmark symptom of COVID-19. More expansive symptom tracking could help to contain the spread of COVID-19.

Risk of COVID-19 among Elderly and Significance of Hypertension

Individuals older than 65 are overrepresented in the composition of COVID-19 infection, hospitalization, ICU admission, and death. The greater risk COVID-19 that poses to the elderly has greatly contributed to social distancing and the implementation of other public health measures intended to slow the spread of the disease. The strong correlation between hypertension and COVID-19 is believed to play a central role in the overrepresentation of the elderly among infected patients. 63.1% of adults above the age of 60 are hypertensive, and many in this patient population use Angiotensin Converting Enzyme (ACE) inhibitors to lower their blood pressure. Sustained use of ACE inhibitors may serve to increase expression of the ACE-2 receptor in the cardiovascular, renal, gastrointestinal, and pulmonary organ systems. Because SARS-CoV-2 is believed to enter cells through the ACE-2 receptor, the upregulation of ACE-2 in hypertensive patients, who are disproportionately elderly, could serve to increase their disease burden.

COVID-19 and Hospital Transmission for High-Risk Patients

Dr. Shu-Yuan Xiao, a gastroenterologist affiliated with the University of Chicago School of Medicine, studied two patients in Zhongnan hospital in Wuhan, China. The patients, undergoing lung lobectomies for adenocarcinoma, were found to have COVID-19 during the surgery. Pathology reports revealed that both patients had pulmonary edema and inflamed alveoli, both characteristic of pneumonia. At the time of the surgery, neither patient exhibited symptoms of pneumonia, suggesting that patients remained in an early phase of the disease progression. The unexpected cases of pneumonia in a patient population reporting for a surgical procedure for a non-COVID condition illustrates the risk of asymptomatic patients serving as vectors for healthcare providers and other patients in the hospital. To counteract the spread of COVID-19 within healthcare settings, aggressive monitoring of symptoms is desirable, to isolate patients suspected to be positive.

Silent Hypoxia: A Clinical Conundrum

Hypoxemia refers to below-average blood oxygenation, while hypoxia is the clinical state of diminished tissue oxygen tension. Clinically, normal arterial blood oxygen saturation is designated as between 94% and 100%. Reduced blood and tissue oxygenation can disrupt cellular metabolism, growth, and development. Healthcare professionals have traditionally understood hypoxia to be coincident with symptoms of respiratory distress, such as shortness of breath. The clinical presentation of COVID-19, however, partly contradicts this understanding. Dr. Richard Levitan, a volunteer emergency medical provider at Bellevue Hospital in New York, reports cases in which patients, despite having undergone imaging that confirmed viral pneumonia and sub-average blood oxygen saturation, did not report respiratory discomfort for several days before presenting at a hospital. Such cases document a phenomenon referred to as "silent hypoxia." referenced above Classification levels for hypoxemia are presented in the following table:

| CLASSIFICATION OF HYPOXEMIA | | |
| --- | --- | --- |
| Classification | PaO$_2$ (mmhg) | SaO$_2$ (%) |
| Normal | 80-100 | >95 |
| Mild Hypoxemia | 60-70 | 90-94 |
| Moderate Hypoxemia | 40-59 | 75-89 |
| Severe Hypoxemia | <40 | <75 |

COVID-19 binds to receptors on alveolar cells, which produce surfactant. Surfactant breaks up the surface tension of water within the alveoli, thereby preventing the alveolar space from collapsing following exhalation. Infection contributes to reduced surfactant production and collapsed air spaces. White blood cells, or leukocytes, mount an inflammatory response within the alveoli. Leukocytes also release cytokines which promote fluid leakage from the pulmonary microvasculature into the space around the alveoli. The buildup of fluid also contributes to the alveolar collapse. Alveolar collapse reduces the interface for oxygen to diffuse into the bloodstream, contributing to hypoxemia. At this stage in disease progression, the lung's compliance may remain unchanged. Consequently, patients may still be able to exhale normal amounts of carbon dioxide, which prevents the onset of breathlessness—making them "silently hypoxic." In certain cases, the buildup of fluid and inflammation can progress to a point in which total lung volume decreases, which impedes the clearance of carbon dioxide and results in breathlessness. This transition can be rapid and necessitate ventilatory assistance, which can burden the healthcare system in the aggregate.

COVID-19 and ARDS

Acute respiratory distress syndrome (ARDS) is characterized by the acute development of pulmonary edema, hypoxia, and a subsequent reliance on mechanical ventilation. ARDS is a prominent cause of respiratory failure and was evident in 10% of patients in ICUs prior to the emergence of COVID-19. Unlike cases of silent hypoxia, ARDS is associated with diminished exhalation of carbon dioxide, which contributes to increased shortness of breath. Severe injury to the alveolar cells of the lung contributes to ARDS. Alveolar damage results in an increase in alveolar permeability to fluid—a process that is mediated by inflammatory signals known as cytokines. Disease progression can lead to widespread pulmonary scarring and adverse changes in lung compliance.

ARDS has particular relevance with respect to COVID-19. A retrospective clinical study of 107 patients in Wuhan, China, indicated that 26.2% of all COVID patients had developed ARDS. Among deceased COVID patients, 78.9% had reported ARDS. Another Wuhan clinical study indicates that patients developed ARDS between 8 and 15 days after the onset of illness. The seemingly benign hypoxia in "silent hypoxia" can progress to ARDS, which can be fatal for COVID patients. As such, robust monitoring of blood oxygen saturation can alert patients of hypoxia before the onset of ARDS, potentially improving outcomes and helping providers organize care.

Clinical Management of ARDS

Severe inflammation and fluid accumulation within the lungs of ARDS patients can result in advanced lung fibrosis potentially culminating in total lung collapse. According to the American Thoracic Society, ARDS is associated with a 30-40% mortality rate. Among patients who recover, lung function can gradually recover in a process that can take between six months to a year. Such recovery is only partial, however, as surviving patients will have below-average lung volume and remaining lung fibrosis. According to Dr. Gregory Cosgrove, Chief Medical Officer of the Pulmonary Fibrosis Foundation, patients who survive ARDS can have reduced quality of life which can contribute to anxiety, depression, and/or PTSD. Thus, it is desirable for clinical workflows to include symptom monitoring to rapidly identify patients whose mild COVID-19 symptoms may progress to more severe states such as ARDS.

Clotting and Silent Hypoxia

With increased awareness regarding silent hypoxia in COVID-19 patients, theories have emerged regarding the origin of the phenomenon which seems to contradict medical convention. Dr. Elnara Marcia Negri, a pulmonologist in Sao Paulo, Brazil, emphasizes the role of clotting in inducing a silent hypoxic state in COVID-19 patients. According to Negri, an inflammatory reaction within the pulmonary vasculature may result in subtle increases in blood clot formation in patients with COVID-19. Increased clot formation would interfere with the diffusion of oxygen from the alveoli into the bloodstream, resulting in hypoxia. Negri administered heparin, a common anticoagulant, to patients with hypoxia, regardless of whether they experienced symptoms. According to Negri, 24 of 27 patients have recovered, lending support to her theory. Negri advises patients to routinely monitor their blood oxygen saturation levels, visiting the hospital in the event that their blood oxygen saturation levels dip below 93%.

Hypoxic Strokes in COVID-19

Large-vessel stroke is a condition in which blood flow in one of the major arteries perfusing the brain becomes interrupted. Interrupted blood flow reduces the availability of oxygen in the brain. Physicians affiliated with the Mount Sinai Health System in New York reported five cases of stroke in COVID-19 positive patients below the age of 50 years old. Furthermore, a retrospective study of data from Wuhan indicates that the incidence of stroke among COVID-19 patients was approximately 5%.

Additionally, the average age of COVID-19 patients afflicted with strokes in Wuhan was 55 years, suggesting that COVID-19-related strokes pose a distinctive risk to a slightly younger patient population. Physicians attribute the incidence of strokes in COVID-19 patients to the role the infection plays in inducing dysfunction in endothelial cells, which line the interior of blood vessels. The association of COVID-19 with other serious pathologies, such as large-vessel strokes, underscores the desirability of robust monitoring of blood oxygen saturation.

Shortcomings in Known COVID-19 Diagnostic Technology

Cleveland Clinic researchers have investigated the efficacy of existing diagnostic technology used to identify patients who are positive for COVID-19. These diagnostic tests include Abbott's ID NOW machine, which has been said to produce results in under 15 minutes. According to the study, the ID NOW had a false-negative rate of 14.8% and a true positive rate of 85.2%. The study's results suggest that approximately 15% of positive patients would falsely be labeled as being uninfected with the ID NOW test. The study also investigated the DiaSorin Simplexa test, which had a true-positive rate of 89.3%. According to Dr. Gary Procop, head of COVID-19 testing at the Cleveland Clinic, diagnostic tests should have true-positive rates of at least 95% to assure the public of the test's efficacy. Although diagnostic platforms made by Roche and Cepheid had accuracy rates above 95%, the subthreshold accuracy of the DiaSorin Simplexa and ID NOW platforms suggest that there are lingering inadequacies within areas of diagnostics for COVID-19. The challenges within COVID-19 testing render the monitoring of other clinical variables, like blood oxygen saturation, even more important. It is possible that robust oxygen monitoring could be used to supplement traditional nasopharyngeal swab tests to yield an even higher accuracy of COVID-19 diagnosis, quickly identifying patients who need medical assistance.

Known Monitoring Solutions to Combat Silent Hypoxia—Pulse Oximetry

Given the possibility that a patient may experience severe hypoxia prior to the onset of breathlessness, some medical providers have called for widespread pulse oximetry. Pulse oximetry can provide patients with a non-invasive way to monitor their blood oxygen saturation levels, alarming them of hypoxia even if they report no other symptoms. A pulse oximeter includes a light emitting sensor that can be clipped to a patient's finger. Patients using at-home pulse oximeters may consult their medical providers, facilitating proper interpretation of blood oxygen saturation levels. Dr. Levitan, an emergency medical physician at Bellevue hospital who noted cases of silent hypoxia, has called for all COVID-19 positive patients to routinely check their blood oxygen saturation levels within the two weeks following diagnosis. Oxygenation monitoring for patients that have not been diagnosed, yet have symptoms of cough, fatigue, and/or fever, may also be prudent Known pulse oximeters, such as finger clips, can be useful for patient assessment, but are often difficult to transport and/or use. Some pulse oximeters, such as the Nonin Onyx, are bulky and can fall off during patient transport or as a result of routine daily movements such as getting up, sitting down, and wiggling one's fingers. In addition, some patients may have a weak pulse or tissue damage, which can skew measurement results. Other known wearable devices provide measurements only at the wrist, and such devices typically do not provide oxygen monitoring or associated warnings. Rather, such devices measure pulse and fitness-related measurements such as step count and sleep time.

In the case of COVID-19, the pulse oximeter finger cuff typically does not provide and/or is not used for continuous monitoring. In cases of silent hypoxia, when patients do not feel any respiratory distress, it may not occur to patients to check their blood oxygen saturation levels, and be unaware of their hypoxia for extended periods of time.

As discussed above, blood oxygen saturation is a valuable biomarker of COVID-19, both for symptomatic and asymptomatic individuals. Embodiments of the wearable oxygen monitor set forth herein facilitate the continuous monitoring of blood oxygen saturation levels, via measurements taken on a wearer's ear (e.g., the helix, scapha, pinna, etc.), with relevant measurement data displayed via a mobile software application. When the wearer's SpO2 levels drop below acceptable levels, an alarm is generated and communicated to the wearer (e.g., via one or more of: an audio indication, a light indication, a GUI display, etc.). In addition, the wearer can trigger a call to emergency services by clicking a button on the wearable oxygen monitor.

All combinations of the foregoing concepts and additional concepts discussed herewithin (provided such concepts are not mutually inconsistent) are contemplated as being part of the subject matter disclosed herein. The terminology explicitly employed herein that also may appear in any disclosure incorporated by reference should be accorded a meaning most consistent with the particular concepts disclosed herein.

The drawings are primarily for illustrative purposes, and are not intended to limit the scope of the subject matter described herein. The drawings are not necessarily to scale; in some instances, various aspects of the subject matter disclosed herein may be shown exaggerated or enlarged in the drawings to facilitate an understanding of different features. In the drawings, like reference characters generally refer to like features (e.g., functionally similar and/or structurally similar elements).

The entirety of this application (including the Cover Page, Title, Headings, Background, Summary, Brief Description of the Drawings, Detailed Description, Embodiments, Abstract, Figures, Appendices, and otherwise) shows, by way of illustration, various embodiments in which the embodiments may be practiced. The advantages and features of the application are of a representative sample of embodiments only, and are not exhaustive and/or exclusive. Rather, they are presented to assist in understanding and teach the embodiments, and are not representative of all embodiments. As such, certain aspects of the disclosure have not been discussed herein. That alternate embodiments may not have been presented for a specific portion of the innovations or that further undescribed alternate embodiments may be available for a portion is not to be considered to exclude such alternate embodiments from the scope of the disclosure. It will be appreciated that many of those undescribed embodiments incorporate the same principles of the innovations and others are equivalent. Thus, it is to be understood that other embodiments may be utilized and functional, logical, operational, organizational, structural and/or topological modifications may be made without departing from the scope and/or spirit of the disclosure. As such, all examples and/or embodiments are deemed to be non-limiting throughout this disclosure.

Also, no inference should be drawn regarding those embodiments discussed herein relative to those not discussed herein other than it is as such for purposes of reducing space and repetition. For instance, it is to be understood that the logical and/or topological structure of any combination of any program components (a component collection), other components and/or any present feature sets as described in the figures and/or throughout are not limited to a fixed operating order and/or arrangement, but rather, any disclosed order is exemplary and all equivalents, regardless of order, are contemplated by the disclosure.

The term "automatically" is used herein to modify actions that occur without direct input or prompting by an external source such as a user. Automatically occurring actions can occur periodically, sporadically, in response to a detected event (e.g., a user logging in), or according to a predetermined schedule.

As used herein, the term "substantially" has a meaning similar to "mostly" or "to a great extent." For example, the phrase "a substantially uniform thickness" refers to a thickness value plus or minus a range of 10%.

The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The term "processor" should be interpreted broadly to encompass a general purpose processor, a central processing unit (CPU), a microprocessor, a digital signal processor (DSP), a controller, a microcontroller, a state machine and so forth. Under some circumstances, a "processor" may refer to an application specific integrated circuit (ASIC), a programmable logic device (PLD), a field programmable gate array (FPGA), etc. The term "processor" may refer to a combination of processing devices, e.g., a combination of a DSP and a microprocessor, a plurality of microprocessors, one or more microprocessors in conjunction with a DSP core or any other such configuration.

The term "memory" should be interpreted broadly to encompass any electronic component capable of storing electronic information. The term memory may refer to various types of processor-readable media such as random access memory (RAM), read-only memory (ROM), non-volatile random access memory (NVRAM), programmable read-only memory (PROM), erasable programmable read only memory (EPROM), electrically erasable PROM (EEPROM), flash memory, magnetic or optical data storage, registers, etc. Memory is said to be in electronic communication with a processor if the processor can read information from and/or write information to the memory. Memory that is integral to a processor is in electronic communication with the processor.

The terms "instructions" and "code" should be interpreted broadly to include any type of computer-readable statement(s). For example, the terms "instructions" and "code" may refer to one or more programs, routines, subroutines, functions, procedures, etc. "Instructions" and "code" may comprise a single computer-readable statement or many computer-readable statements.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Some embodiments and/or methods described herein can be performed by software (executed on hardware), hardware, or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including C, C++, Java™, Ruby, Visual Basic™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

Various concepts may be embodied as one or more methods, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments. Put differently, it is to be understood that such features may not necessarily be limited to a particular order of execution, but rather, any number of threads, processes, services, servers, and/or the like that may execute serially, asynchronously, concurrently, in parallel, simultaneously, synchronously, and/or the like in a manner consistent with the disclosure. As such, some of these features may be mutually contradictory, in that they cannot be simultaneously present in a single embodiment. Similarly, some features are applicable to one aspect of the innovations, and inapplicable to others.

In addition, the disclosure may include other innovations not presently described. Applicant reserves all rights in such innovations, including the right to embodiment such innovations, file additional applications, continuations, continuations-in-part, divisionals, and/or the like thereof. As such, it should be understood that advantages, embodiments, examples, functional, features, logical, operational, organizational, structural, topological, and/or other aspects of the disclosure are not to be considered limitations on the disclosure as defined by the embodiments or limitations on equivalents to the embodiments. Depending on the particular desires and/or characteristics of an individual and/or enterprise user, database configuration and/or relational model, data type, data transmission and/or network framework, syntax structure, and/or the like, various embodiments of the technology disclosed herein may be implemented in a manner that enables a great deal of flexibility and customization as described herein.

All definitions, as defined and used herein, should be understood to control over dictionary definitions, definitions in documents incorporated by reference, and/or ordinary meanings of the defined terms.

As used herein, in particular embodiments, the terms "about" or "approximately" when preceding a numerical value indicates the value plus or minus a range of 10%. Where a range of values is provided, it is understood that each intervening value, to the tenth of the unit of the lower limit unless the context clearly dictates otherwise, between the upper and lower limit of that range and any other stated or intervening value in that stated range is encompassed within the disclosure. That the upper and lower limits of these smaller ranges can independently be included in the smaller ranges is also encompassed within the disclosure, subject to any specifically excluded limit in the stated range. Where the stated range includes one or both of the limits, ranges excluding either or both of those included limits are also included in the disclosure.

The indefinite articles "a" and "an," as used herein in the specification and in the embodiments, unless clearly indicated to the contrary, should be understood to mean "at least one."

The phrase "and/or," as used herein in the specification and in the embodiments, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the embodiments, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the embodiments, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the embodiments, shall have its ordinary meaning as used in the field of patent law.

As used herein in the specification and in the embodiments, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the embodiments, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. An apparatus, comprising:
a processor and a memory operably coupled to the processor;
a first housing portion including at least one light-emitting diode (LED), the at least one LED including a green LED;
a second housing portion, distinct from the first housing portion and spaced from the first housing portion, the second housing portion including a photodetector; and
a connection member mechanically coupled to each of the first housing portion and the second housing portion,
the at least one LED configured, during operation, to emit light in a direction toward the photodetector, a portion of the emitted light passing through a portion of an ear of a wearer of the apparatus prior to arriving at the photodetector and during operation of the at least one light emitting diode LED and when the apparatus is worn about the portion of the ear,
the photodetector configured to detect the portion of the emitted light,
the memory storing instructions to cause the processor to:
calculate a blood oxygen saturation level of the wearer based on the detection of the portion of the emitted light; and
cause a vibration of the first housing portion and the second housing portion in response to detecting that the blood oxygen saturation level is below a defined threshold value.

2. The apparatus of claim 1, wherein the photodetector is a first photodetector and the portion of the emitted light is a first portion of the emitted light, the first housing portion further including a second photodetector configured to detect a second, reflected, portion of the emitted light, the memory further storing instructions to cause the processor to calculate the blood oxygen saturation level of the wearer based on the detection of the first portion of the emitted light and the detection of the second portion of the emitted light.

3. The apparatus of claim 1, further comprising at least one of a microphone or a speaker operatively coupled to the processor, the memory further storing instructions to cause the processor to activate the at least one of the microphone or the speaker in response to detecting an alarm condition.

4. The apparatus of claim 1, further comprising a wireless transceiver, operatively coupled to the processor and configured to communicate with a mobile software application, the memory further storing instructions to cause the processor to send signals representing measurement data to the mobile software application via the wireless transceiver.

5. The apparatus of claim 1, wherein the memory further stores instructions to cause the processor to send signals, according to a predetermined schedule, to a mobile software application, the signals representing measurement data.

6. The apparatus of claim 1, further comprising at least one sensor operatively coupled to the processor, the at least one sensor including at least one of: a body temperature sensor, an air quality sensor, a humidity sensor, an altimeter, or a barometric pressure sensor, the memory further storing instructions to cause the processor to store, in the memory, data collected by the at least one sensor.

7. The apparatus of claim 1, further comprising at least one sensor operatively coupled to the processor, the at least one sensor including at least one of: a body temperature sensor, an air quality sensor, a humidity sensor, an altimeter, or a barometric pressure sensor, the memory further storing instructions to cause the processor to send signals, according to a predetermined schedule, to a mobile software application, the signals representing data collected by the at least one sensor.

8. The apparatus of claim 1, wherein the at least one LED includes a red LED, an infrared LED, and the green LED.

9. The apparatus of claim 1, wherein the at least one LED includes:
a first LED configured to emit light having a first wavelength compatible with transmissive sensing; and
a second LED configured to emit light having a second wavelength, the second wavelength being different from the first wavelength and compatible with reflective sensing.

10. The apparatus of claim 1, wherein the connection member includes a deformable material and is configured to be deformed during positioning of the apparatus about the portion of the ear of the wearer.

* * * * *

UNITED STATES PATENT AND TRADEMARK OFFICE
CERTIFICATE OF CORRECTION

PATENT NO. : 10,987,067 B2
APPLICATION NO. : 16/903732
DATED : April 27, 2021
INVENTOR(S) : Shavini Fernando It is certified that error appears in the above-identified patent and that said Letters Patent is hereby corrected as shown below:

In the Claims

At Column 33, Claim number 1, Line number 44:
"light emitting diode LED and when the apparatus is"

Should read:
-- LED and when the apparatus is --

Signed and Sealed this
Eighth Day of June, 2021

Drew Hirshfeld
*Performing the Functions and Duties of the*
*Under Secretary of Commerce for Intellectual Property and*
*Director of the United States Patent and Trademark Office*